United States Patent [19]

Lorenzen et al.

[11] Patent Number: 5,735,271
[45] Date of Patent: Apr. 7, 1998

[54] MULTIPLE ACCESS ADAPTORS FOR MONITORING, SAMPLING, MEDICATING, ASPIRATING, AND VENTILATING THE RESPIRATORY TRACT OF A PATIENT

[75] Inventors: Rick D. Lorenzen, Ogden; Darrel R. Palmer, Sandy; William R. Houghton, Midvale; Gerry A. Arambula; David Theron Van Hooser, both of Salt Lake City; Richard C. Lambert, Highland; Billy M. Jensen, Sandy; Gene Stewart, Midvale, all of Utah

[73] Assignee: Ballard Medical Products, Draper, Utah

[21] Appl. No.: 653,938

[22] Filed: May 22, 1996

Related U.S. Application Data

[63] Continuation of Ser. No. 395,351, Feb. 28, 1995, abandoned, and Ser. No. 591,950, Jan. 23, 1996, which is a continuation of Ser. No. 245,333, May 18, 1994, abandoned.

[51] Int. Cl.⁶ ............................. A62B 9/02; A62B 9/06; A61M 16/00
[52] U.S. Cl. ................... 128/207.16; 128/205.24; 128/207.14; 128/205.19; 128/912; 128/200.26
[58] Field of Search .......... 128/200.26, 207.14–207.16, 128/911, 912, DIG. 26, 205.24, 205.19; 604/280, 171

[56] References Cited

U.S. PATENT DOCUMENTS

| | | |
|---|---|---|
| 274,447 | 3/1883 | Kennish . |
| 2,705,959 | 4/1955 | Elmore ........................ 128/351 |
| 2,755,060 | 7/1956 | Twyman ........................ 251/342 |
| 2,912,982 | 11/1959 | Barsky ........................ 128/351 |
| 3,335,723 | 8/1967 | Waldman, Jr. ........................ 128/214.4 |
| 3,444,860 | 5/1969 | Harrell ........................ 128/349 |
| 3,454,005 | 7/1969 | Eubanks et al. ........................ 128/186 |
| 3,517,669 | 6/1970 | Buono et al. ........................ 128/276 |
| 3,614,057 | 10/1971 | Hospe ........................ 251/251 |
| 3,730,179 | 5/1973 | Williams ........................ 128/145.5 |
| 3,757,771 | 9/1973 | Ruegg et al. ........................ 18/2.1 E |
| 3,774,604 | 11/1973 | Danielsson ........................ 182/214.4 |
| 3,794,026 | 2/1974 | Jacobs ........................ 128/145.8 |
| 3,825,001 | 7/1974 | Bennet et al. ........................ 128/214.4 |
| 3,831,629 | 8/1974 | Mackal et al. ........................ 137/525 |
| 3,885,561 | 5/1975 | Cami ........................ 128/214 |
| 3,894,540 | 7/1975 | Bonner, Jr. ........................ 128/349 R |
| 3,902,500 | 9/1975 | Dryden ........................ 128/351 |
| 3,911,919 | 10/1975 | Raitto ........................ 182/276 |
| 3,937,220 | 2/1976 | Coyne ........................ 128/276 |
| 3,991,762 | 11/1976 | Radford ........................ 128/276 |
| 4,022,219 | 5/1977 | Basta ........................ 128/351 |
| 4,050,667 | 9/1977 | Kossett ........................ 249/82 |
| 4,062,363 | 12/1977 | Bonner, Jr. ........................ 128/349 R |
| 4,152,017 | 5/1979 | Abramson ........................ 285/260 |
| 4,170,996 | 10/1979 | Wu ........................ 128/349 R |
| 4,193,406 | 3/1980 | Jinotti ........................ 128/204.18 |
| 4,214,593 | 7/1980 | Imbruce et al. ........................ 128/748 |
| 4,235,232 | 11/1980 | Spaven et al. ........................ 128/214.4 |
| 4,240,417 | 12/1980 | Holever ........................ 128/203.12 |
| 4,256,099 | 3/1981 | Dryden ........................ 128/200.26 |

(List continued on next page.)

Primary Examiner—Kimberly L. Asher
Attorney, Agent, or Firm—Workman Nydegger Seeley

[57] ABSTRACT

Apparatus and methods are disclosed by which a closed ventilating system accommodates multiple access to the respiratory system of an intubated medical patient. Access to the respiratory system is accomplished via one or more access ports through an attached accessory device in order to ventilate the lungs of the patent with gas or gasses, aspirate secretions from the lungs, oxygenate the lungs, visually inspect selected parts of the respiratory system, sample sputum and gasses, sense parameters such as flow rates, pressure, and temperature, flush the respiratory tract with washing solution, and/or administer medication, gasses, and/or lavage. The embodiments of the present invention may have such accessory devices permanently fixed to the adaptor or may be removable and replaceable. Access control means may be provided whereby one or more access ports are selectively aligned with the adaptor in order to allow passage of an attached accessory device therethrough.

38 Claims, 11 Drawing Sheets

U.S. PATENT DOCUMENTS

| | | | |
|---|---|---|---|
| 4,300,550 | 11/1981 | Gandi et al. | 182/207.18 |
| 4,326,520 | 4/1982 | Alley | 128/214.4 |
| 4,327,723 | 5/1982 | Frankhouser | 128/214.4 |
| 4,327,735 | 5/1982 | Hampson | 128/348 |
| 4,333,451 | 6/1982 | Paluch | 128/205.12 |
| 4,351,328 | 9/1982 | Bodai | 128/202.16 |
| 4,387,879 | 6/1983 | Tauschinski | 251/149.1 |
| 4,397,442 | 8/1983 | Larkin | 251/342 |
| 4,440,378 | 4/1984 | Sullivan | 251/117 |
| 4,454,887 | 6/1984 | Krüger | 128/772 |
| 4,456,223 | 6/1984 | Ebling | 251/342 |
| 4,502,482 | 3/1985 | DeLuccia et al. | 182/207.15 |
| 4,510,933 | 4/1985 | Wendt et al. | 128/207.14 |
| 4,512,765 | 4/1985 | Muto | 604/119 |
| 4,534,542 | 8/1985 | Russo | 251/342 |
| 4,569,344 | 2/1986 | Palmer | 128/207.16 |
| 4,607,635 | 8/1986 | Heyden | 128/207.15 |
| 4,634,433 | 1/1987 | Osborne | 604/171 |
| 4,637,389 | 1/1987 | Heyden | 128/207.15 |
| 4,638,539 | 1/1987 | Palmer | 29/157 R |
| 4,646,733 | 3/1987 | Stroh et al. | 182/207.16 |
| 4,655,752 | 4/1987 | Honkanen et al. | 604/256 |
| 4,669,463 | 6/1987 | McConnell | 182/207.14 |
| 4,696,296 | 9/1987 | Palmer | 128/207.16 |
| 4,767,409 | 8/1988 | Brooks | 128/207.14 |
| 4,805,611 | 2/1989 | Hodgkins | 128/207.14 |
| 4,819,664 | 4/1989 | Nazari | 128/207.15 |
| 4,821,714 | 4/1989 | Smesler | 128/207.14 |
| 4,825,859 | 5/1989 | Lambert | 128/202.16 |
| 4,834,726 | 5/1989 | Lambert | 604/281 |
| 4,836,199 | 6/1989 | Palmer | 128/207.16 |
| 4,838,255 | 6/1989 | Lambert | 128/202.16 |
| 4,848,331 | 7/1989 | Northway-Meyer | 128/200.26 |
| 4,850,350 | 7/1989 | Jackson | 128/207.16 |
| 4,872,579 | 10/1989 | Palmer | 128/205.19 |
| 4,938,741 | 7/1990 | Lambert | 604/19 |
| 4,967,743 | 11/1990 | Lambert | 182/202.16 |
| 4,969,878 | 11/1990 | Schmidt et al. | 604/264 |
| 5,029,580 | 7/1991 | Radford et al. | 128/207.14 |
| 5,031,613 | 7/1991 | Smith et al. | 128/207.15 |
| 5,083,561 | 1/1992 | Russo | 128/207.16 |
| 5,088,486 | 2/1992 | Jinotti | 128/207.14 |
| 5,134,996 | 8/1992 | Bell | 182/207.14 |
| 5,140,983 | 8/1992 | Jinotti | 128/207.14 |
| 5,279,549 | 1/1994 | Ranford | 128/207.14 |
| 5,346,478 | 9/1994 | Jinotti | 604/171 |
| 5,354,267 | 10/1994 | Niermann et al. | 128/207.14 |
| 5,431,157 | 7/1995 | Mourkidou et al. | 182/207.14 |
| 5,490,503 | 2/1996 | Hollister | 128/205.12 |

MULTIPLE ACCESS ADAPTORS FOR MONITORING, SAMPLING, MEDICATING, ASPIRATING, AND VENTILATING THE RESPIRATORY TRACT OF A PATIENT

RELATED APPLICATION

This application is a continuation of application Ser. No. 08/395,351 filed Feb. 28, 1995 (now abandoned) entitled "Multiple Access Manifolds, Fittings, Adaptors, and Access Control Devices for Monitoring, Sampling, Medicating, Aspirating, and Ventilating the Respiratory Tract of a Patient and Related Methods," and is also a continuation of application Ser. No. 08/591,950 filed Jan. 23, 1996, entitled "Medical Multiple Access Low Dead Space Anti-Microbial Aspirating/Ventilating Closed System Improvements and Methods," both of which are incorporated herein by reference, application Ser. No. 08/591,950 is a file wrapper continuation of application Ser. No. 08/245,333 filed May 18, 1994 (now abandoned).

BACKGROUND OF THE INVENTION

FIELD OF INVENTION

The inventions disclosed herein relate generally to improved medical care for intubated patients, and more particularly to novel multiple access manifold, fitting, or adaptor and access control device inventions, and related methods, for ventilating, aspirating, monitoring, sampling, and providing therapeutic delivery to the respiratory tracts of intubated medical patients, including infants, adolescents, and adults.

BACKGROUND

Respiratory patient care is a dynamically developing field in medicine, ranging in its needs from infants to the aged. The range of respiratory ailments, both temporary and permanent, to which such patients are subjected, are many and varied. The frontier of medical knowledge is advancing and recommended treatments have become a blend of old and more recent discoveries.

Most problems now center or focus on multiple needs of the patient and accommodation of multiple treatments, some to be performed at the same time. The lack of equipment to facilely, efficiently, and safely accomplish the multiple therapies in the best interest of the patient has been and continues to be a concern. Other equipment problems also exist which concern preventing cost-oriented, unsafe extended use of ventilating, aspirating, and other respiratory access apparatus, reliability during use, quick and reliable removal and exchange of spent aspirating and ventilating devices without compromising the quality of health care provided to the patient, avoiding intentional or inadvertent conversion from a closed system to an open system, prevention of stress and/or occlusion of flow passageways to and from the patient's respiratory system, avoidance of a large inventory of a variety of incompatible products, providing easy, fail-safe access for multiple purposes.

By way of an example only, with low lung capacity patients, such as premature babies and adults suffering from emphysema, one problem is the removal of accumulated lung secretions without starving the patient for oxygen (thereby causing undesirable side effects) during the secretion removal process.

Sight must not be lost as to the deficiencies in prior proposals in terms of risks created for the health care provider. Largely, proposals of the past have ignored the needs of the health care provider to receive a reasonable measure of protection from contamination by the patient.

Providing apparatus and methodology having the capacity to promptly, efficiently, safely, and cost effectively address the health care needs of intubated patients across the entire spectrum of respiratory ailments comprises, prior to the present invention, a largely unresolved need. The range of procedures comprise: ventilating, aspiration, oxygenation, sampling, visual inspection, in-line sensing, pressure monitoring, flushing, and medication and/or lavage. Better protection for the health care provider has been a long-term unsatisfied need.

BRIEF SUMMARY AND OBJECTS OF THE PRESENT INVENTION

In brief summary, the present invention substantially alleviates problems of the prior art and comprises apparatus and methods by which a closed ventilating system accommodates multiple access to the respiratory system of an intubated medical patient without compromising the closed character of the system and without interruption of the flow of ventilating gases to the patient. Access to the respiratory system through one or more access sites of the closed system apparatus is provided to ventilate the lungs of the patient with gas or gases, to aspirate secretions from the lungs, to oxygenate the lungs to eliminate or reduce residual $CO_2$ therefrom, to visually inspect selected parts of the respiratory system, to sample sputum and gases, to sense parameters such as flow rates, pressure, and temperature, to flush with washing solution, and/or to administer medication, gases, and/or lavage.

One system is unitized into severable and disposable components which are cost effective and accommodate good health care practices while promoting limitations on duration of use well within appropriate medical tolerances. Quick removal and replacement of discarded components is accommodated without introduction of additional risks to the patient. The technology of the present invention has substantial universal application to all respiratory patients, ranging from infants to the aged. An accessory device can be added or removed from a manifold, fitting, or adaptor while the associated access port is in an off condition. Novel access control devices in association with an access port of a manifold, fitting, or adaptor accommodate selective enabled and disabled of port of a manifold, fitting, or adaptor for access and non-access and for attachment, detachment, and exchange of accessory devices.

With the foregoing in mind, it is a primary object of the present invention to substantially alleviate problems of the prior art in the field of respiratory care for medical patients.

It is an additional dominant object of the present invention to provide apparatus and related methods by which a closed ventilating system is able to accommodate multiple access to the respiratory system of an intubated medical patient.

An additional paramount object is the provision of novel apparatus and related methods by which a closed ventilating system accommodates multiple access to the respiratory system of an intubated medical patient without compromising the closed character of the system.

An additional object of the present invention is the provision of access through one or more access sites in a closed system respiratory apparatus to accommodate ventilating of the lungs of the patient with gas or gases, to aspirate secretions from the lungs, to oxygenate the lungs to eliminate or reduce residual carbon dioxide therefrom, to visually inspect selected parts of the respiratory system, to sample sputum and gases, to sense parameters such as flow rates, pressure, and temperature, to flush with washing solution and/or to administer medication, gases, and/or lavage, and related methods.

An additional significant object is the provision of a closed respiratory health care system unitized into severable and disposable components which are cost effective and accommodate good health care practices while promoting limitations on duration of use well within appropriate medical tolerances.

It is an additional valuable object to provide for quick removal and replacement of discardable components toward the end of their useful life in a respiratory health care system and to accommodate such without introduction of additional risks to the patient.

It is another dominant object to provide a respiratory health care system and related methods which has substantial universal application to all respiratory patients ranging from infants to the aged.

It is a further object of significance to provide a respiratory health care system and related methods by which superior protection is provided by the care giver to an intubated patient.

It is a further object of the present invention to provide novel respiratory systems and related methods comprising a plurality of entry sites normally sealed to minimize introduction of contamination and avoid loss of ventilating gas or pressure, but yet to allow selective entry of an instrument, device, or the like.

It is a primary object of the present invention to provide a unitized respiratory health care system and related method where components of the system comprise disposable segments which may be facilely connected and removed by the care giver.

A further important object of the present invention is to provide features in a respiratory health care system which avoid imposition of stress on the components and prohibit occlusion of flow pathways.

It is a prominent object of the present invention to provide respiratory health care systems and related methods which accommodate simultaneous access to and treatment within the respiratory system of a medical patient.

It is a further object of the present invention to provide novel respiratory health care systems and related methods having minimal dead space.

Still another paramount object is the provision of a mechanism and related methods to provide access and non-access of one or more accessory devices to the interior of a manifold, fitting, or adaptor.

Still a further valuable object is the provision of novel access port control devices and related methods by which accessory devices are selectively placed in and out of communication with the access port of a manifold, fitting, or adaptor.

Another object of significance is the provision of novel manifold access port control devices and related methods by which a connector site of the control device can be disabled to accommodate attachment, detachment, non-use, or exchange of accessory devices and which can be enabled for use of an attached ancillary device in respect to the access port of the manifold, fitting, or adaptor.

A further object is the provision of novel access control appliances in the nature of unique plugs for access ports which accommodate various accessory devices, the distal ends of which may comprise differing diameters.

These and other objects and features of the present invention will be apparent from the detailed description taken with reference to the accompanying drawings.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawing depict only a typical embodiment of the invention and are not therefore to be considered to be limiting of its scope, the invention will be described and explained with additional specificity and detail through the use of the accompanying drawings in which.

DETAILED DESCRIPTION OF THE ILLUSTRATED EMBODIMENTS

Reference is now made to the drawings wherein like numerals are used to designate like parts throughout.

Figure 1:
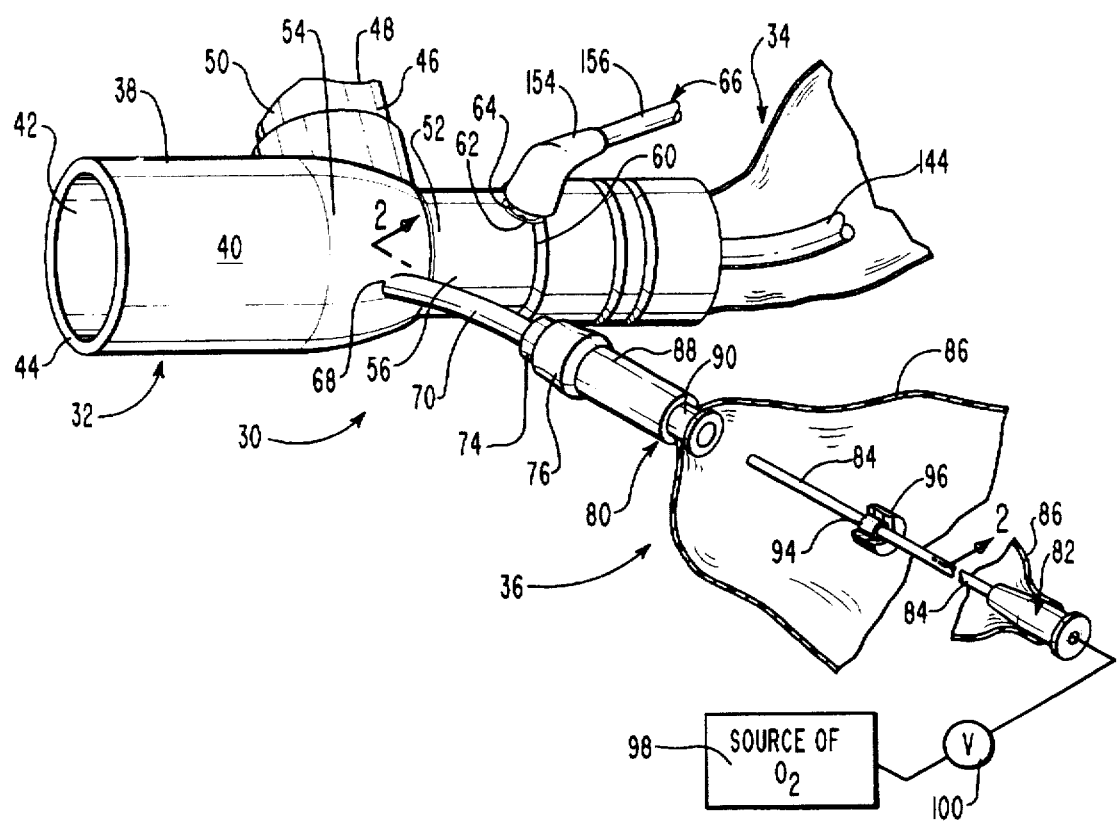
FIG. 1 is a perspective representation of one multi-access embodiment of the present invention with parts broken away and other parts removed for clarity.
Figure 2:
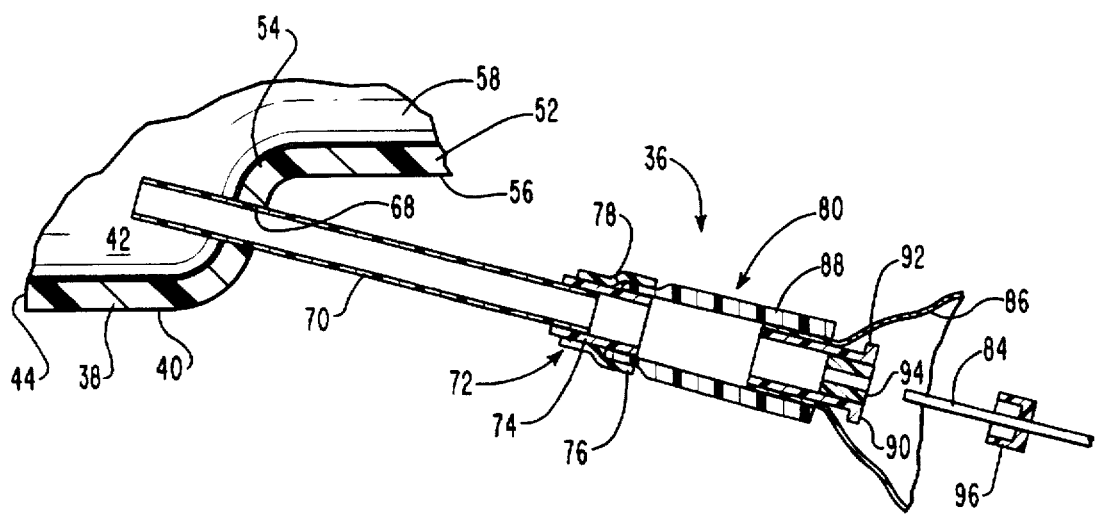
FIG. 2 is an enlarged fragmentary cross section of FIG. 1.

Reference is now made to FIGS. 1 and 2, which illustrate a multiple access apparatus, generally designated 30, embodying principles in accordance with the present invention. Apparatus 30 comprises a T-shaped, elbow-like housing, generally designated 32, an aspirating catheter assembly 34, permanently assembled with the housing 32, and a second catheter assembly, generally designated 36, also permanently connected with the housing 32.

Elbow fitting 32 comprises a cylindrical wall 38, illustrated as being of uniform thickness and comprising exterior surface 40, interior surface 42, and distal edge 44, which interior surface defines a distal port through which ventilating gases are delivered to the patient, when connected to a tracheal tube, for example.

Elbow fitting 32 also comprises a proximal port or barrel 46 comprising a hollow interior into which influence ventilating gases are delivered from a suitable commercially available ventilator. Barrels 38 and 46 are formed as one piece from a suitable synthetic resinous material. The wall 48 comprises a hollow interior defined by an annular interior surface. Wall 48 is preferably of uniform thickness and comprises exterior cylindrical surface 50. The hollow interior of barrel 46 receives ventilating gases from a ventilator and is in open communication with the hollow interior defined by surface 42.

The fitting 32 also comprises a plurality of access ports, one of which is formed by a third (second proximal) barrel 52, the interior of which is also hollow and in direct open communication with the hollow interior formed by wall surface 42. A tapered rounded transitional hollow segment 54 connects wall segment 38 with the wall comprising barrel 52. The wall forming barrel 52 comprises an exterior surface 56 and an interior surface 58 (FIG. 2) and terminates in a proximal edge 60. Edge 60 is radially-directed and annular in its configuration, being interrupted by a notch 62, the diametrical size of which is selected to accommodate positioning of the transverse tube 64 of the attachment 66 of the aspirating catheter assembly 34 therein. The structure and use of the aspirating catheter assembly 116 and more particularly the aspirating catheter tube 144 thereof to aspirate secretions from the lungs of a patient is described below.

In order to enlarge the number of respiratory access ports available, an additional access port can be readily provided in adaptor 32. This may be done by boring or otherwise forming an aperture or access port 68 at the step or transition segment 54 of bell housing 38. While aperture 68 is illustrated as being disposed in a particular diagonal orientation, it is to be appreciated that the direction of aperture 68 in transition wall 54 may be selected, as desired, by those skilled in the art.

The tube 70 having an exterior surface the diameter of which is just slightly smaller than aperture 68 is inserted a desired although short distance into the hollow interior formed by wall surface 42 and is cemented, bonded, plastic welded, or otherwise secured in the inserted position, in the manner typified in FIG. 2. The proximal end of the tube 70 is equipped with a female fitting, generally designated 72. Fitting 72 comprises a sleeve 74 bonded or otherwise suitably connected to the proximal end of tube 70. A bell-shaped housing 76 is secured to the sleeve 74 in telescopic bonded or otherwise non-rotatably secured position such that the enlarged region of bell housing 76 defines a female annular groove 78. A second catheter assembly 36 for providing other treatment is permanently placed within recess 78, as explained in greater detail hereinafter.

Catheter assembly 36 comprises a distal fitting, generally designated 80, a proximal fitting, generally designated 82, and a catheter treatment tube 84 spanning between the two fittings and encapsulated by a collapsible sheath 86.

Distal fitting 80 comprises a distal collar 88, which is distally tapered to form a reduced diameter tip that is sized, shaped, and dimensioned so as to accommodate being fit into annular slot 78 and bonded or otherwise permanently secured in that position. Collar 88 comprises an interior cylindrical surface into which a distal end of the collapsible sheath 86 is extended at the proximal end thereof, as illustrated in FIG. 2. A fitting 90 is force-fit into the proximal end of the collar 88, being so dimensioned as to hold the distal end of the collapsible sheath 86 in position against inadvertent removal. Fitting 90 comprises a tubular member, which has a uniform cylindrical interior surface throughout. The tubular member comprises an outwardly directed radially-extending flange 92 at the proximal end thereof, the flange 92 having a predetermined diameter at annual periphery.

A sleeve 94 is force-fit into the proximal end of fitting 90 (FIG. 2) so that the proximal edge thereof is flush with the proximal edge of flange 92. The interior surface of sleeve 94 defines a cylindrical passageway diametrically sized so as to snugly receive catheter treatment tube 84 in slidable, wiping relation.

A cup-shaped friction lock 96 surrounds the catheter treatment tube 84 proximally of fitting 90. Lock 96 is preferably cup-shaped with a central aperture that is substantially the same diameter as the outside diameter of catheter tube 84. The interior diameter of friction lock 96 is slightly less than the outside diameter of flange 92. Accordingly, when friction lock 96 is advanced over flange 92, the walls of friction lock 96 are biased outward, which creates a pinching or torque action by the central aperture upon the exterior surface of tube 84. Thus, when catheter treatment tube 84 has been advanced into the respiratory tract of the patient the desired distance, the location of the distal end of the catheter treatment tube may be preserved in said inserted position by holding the catheter treatment tube 84 in the desired position through collapsible sheath 86 and, also through collapsible sheath 86 advancing friction lock 96 until it is superimposed over flange 92. Thus, the pinching action of the central aperture against the exterior surface of the catheter treatment tube 84 will thereafter retain the catheter tube 84 in the predetermined inserted position.

In the alternative, sleeve 94 can be formed of a compressible material with the outside diameter of sleeve 94 being greater, when unstressed, than the inside diameter of fitting 90. The inside diameter of sleeve 94, when unstressed, can be substantially the same as the outside diameter of catheter treatment tube 84. The catheter treatment tube 84 is inserted to the desired location in the respiratory tract while the sleeve 94 is in the position of FIG. 1. Once the desired indwelling location is reached, the sleeve 94 is advanced along the catheter tube 84 and compression fit into the hollow interior of fitting 90, thereby stress or compression reducing both the inside and the outside diameters of sleeve 94. This, in effect, causes sleeve 94 to clamp against the exterior surface of catheter tube 84, holding it in the desired inserted position against inadvertent displacement. The catheter treatment tube 84 may be unclamped simply by removing sleeve 94 from the hollow bore of fitting 90.

The proximal fitting 82 of catheter cartridge 36 comprises a female hub having a hollow interior to which oxygen is communication from source 98 when valve 100 is in the open position.

As illustrated in FIG. 1, the proximal end of sheath 86 is bonded, plastic welded, or otherwise suitably secured to the exterior surface of fitting 82. Fitting 82 is hollow so that oxygen will be communicated along the hollow interior of catheter treatment tube 84 into the respiratory tract of the patient. It is to be appreciated that catheter assembly 36, in lieu of being provided for delivery of oxygen, may be constructed to deliver lavage or medication to the patient or any of the other treatment identified in the summary section of this application including visually inspect selected parts of the respiratory system, to sample sputum and gasses, to sense parameters such as flow rates, pressure and temperature and/or to flush with washing solution as desired using the access site made available by the formation of access port 68 in adaptor 32.

Figure 3:
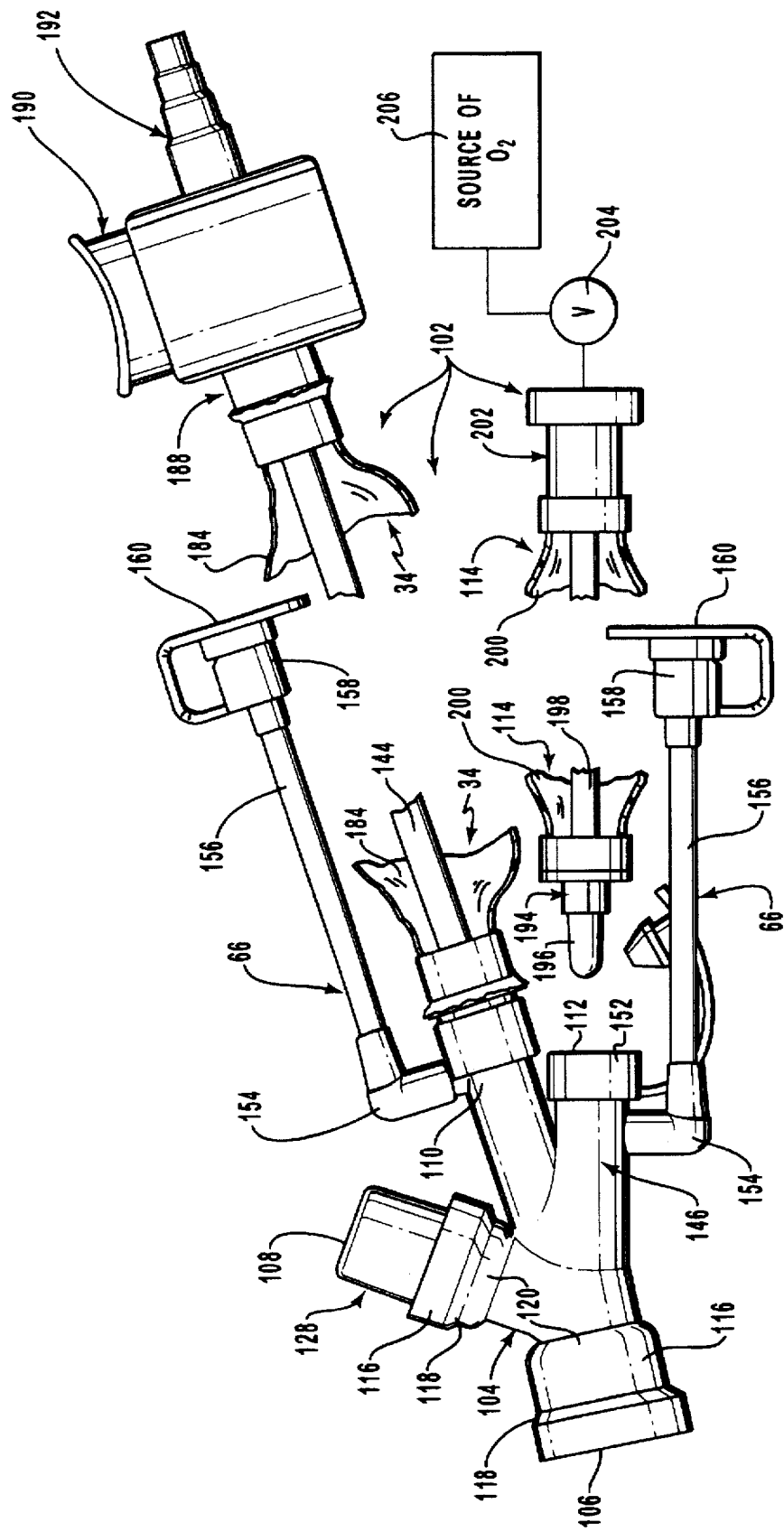
FIG. 3 is a fragmentary side elevation of another multi-access embodiment of the present invention.
Figure 4:
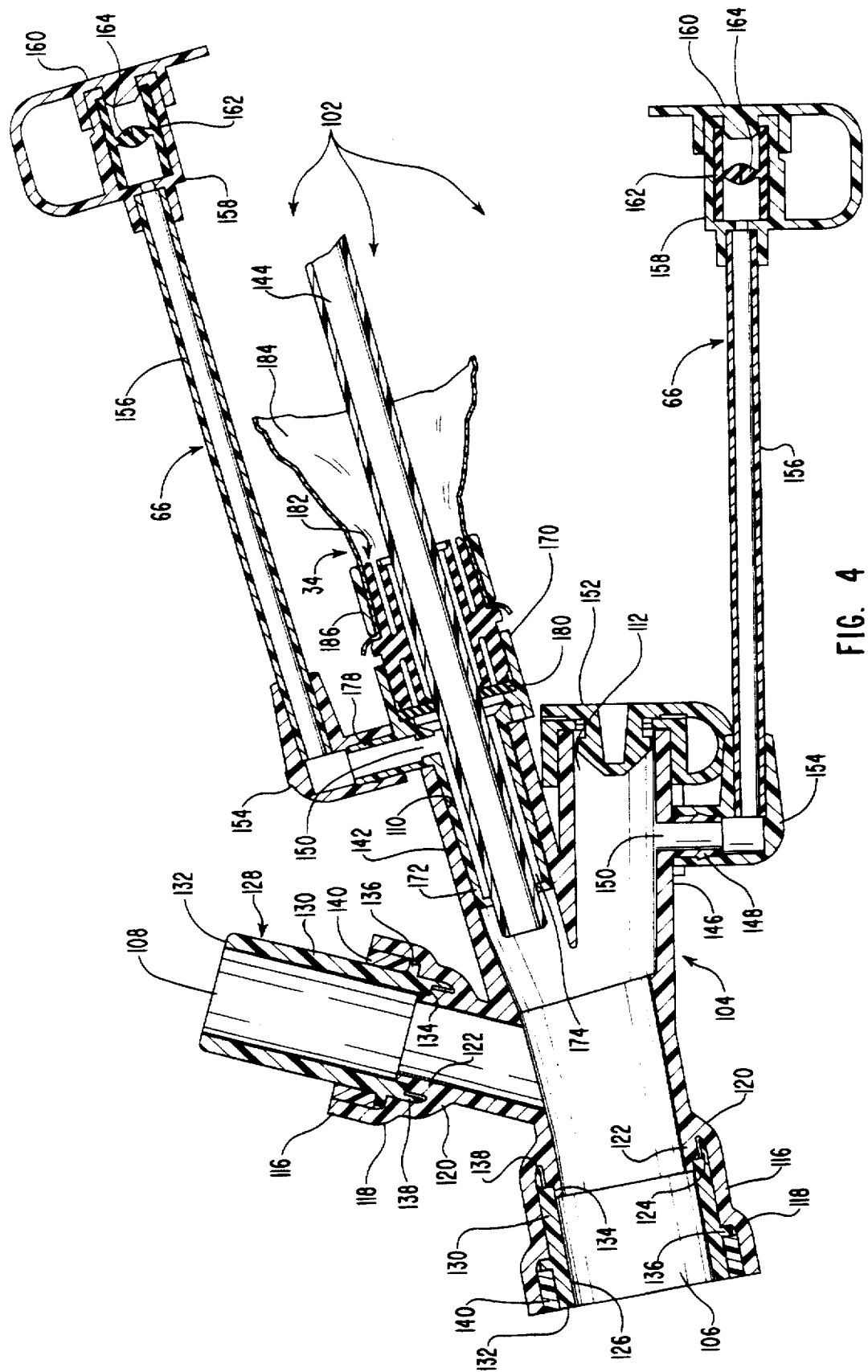
FIG. 4 is a longitudinal cross section of one multi-access embodiment of the present invention.

FIGS. 3 and 4 illustrate a second embodiment of a multi-access apparatus, generally designated 102, for use in conjunction with the respiratory tract of an intubated medical patient ranging from infants to the aged. Like the previous embodiment illustrated in FIGS. 1 and 2, the embodiment shown in FIGS. 3 and 4 has multiples access ports to provide multiple respiratory therapies through catheter assemblies or cartridges, but unlike the embodiment shown in FIGS. 1 and 2, the embodiment illustrated in FIGS. 3 and 4 is designed to have the catheter cartridges removably connected to some of the access ports.

The apparatus 102 comprises adaptor means for defining a flow path therethrough for delivery of ventilating gases to an intubated patient and for providing an access path for delivery of respiratory therapy to the patient. In FIGS. 3 and 4 such adaptor means comprises adaptor 104 having a distal port 106, a proximal port 108 and a plurality of access ports 110, 112 and 150. For example only distal port 106 and proximal port 108 accommodate continual cyclic patient ventilation, independent of pursuit by the health care provider of any other patient respiratory access procedure. Access port 110 accommodates selective insertion and subsequent removal of an aspirating catheter assembly, the catheter tube of which removes secretions from the lungs. Access port 112 accommodates releasable attachment and subsequent removal of other catheter means such as an oxygenation catheter assembly, such as oxygenation catheter cartridge 114, the catheter tube of which is used to replace residual carbon dioxide in the lungs with oxygen, or to accommodate entry of temperature or pressure monitoring instruments or to accommodate obtaining samples of sputum or gases and/or to allow insertion of visual inspection instruments. All these catheter assemblies and other instruments are examples of catheter device means for providing respiratory therapy through the adaptor means.

Referring now to FIGS. 3 and 4 together, the apparatus 102 comprises a tracheal tube adaptor, generally designated 104, preferably formed of injection molded rigid medical grade synthetic resinous material, such as acrylic, cryolite, pebax, polypropylene, or the like. Adaptor 104 comprises a distal port 106 formed from a hollow female distal bell housing which comprises a stepped annular wall 116.

Wall 116 comprises a thickness which is generally uniform. The distal end of wall 116 is defined by a blunt transverse annular distal edge, where the bell housing comprises its largest diameter. Wall 116 comprises a first reduced diameter annular step 118 comprising an inside shoulder, and a second further reduced diameter annular step 120.

Annular step 120 defines a bifurcation where an annular swivel alignment retaining wall 122 extends distally from the bifurcation with wall 116 adjacent step 120. Walls 116 and 122, where co-extensive, are separated by a blind annular slot which opens distally. Walls 116 and 122 are illustrated as being formed as one-piece. Wall 122 comprises an interior surface, illustrated as being of uniform diameter, an exterior surface and a blunt annular transverse distal edge. Wall 62 is stepped or notched at shoulder 124.

Adaptor 104 also comprises a proximal port 108 formed from a second bell housing which is constructed to comprise components the same as the bell housing forming distal port 106, although the bell housing forming proximal port 108 is somewhat shorter in its axial length. Accordingly, the parts of the two bell housings have been enumerated the same and no further description is needed for one skilled in the art.

In order to provide swivel couplings to ventilation tubing and to the intubated patient, embodiments may comprise sleeve means for providing a swivel coupling for joining the adaptor means to the ventilator tubing and the intubated patient. In FIGS. 3 and 4 such sleeve means comprises sleeve 126 and sleeve 128. Sleeve 126 is rotatably positioned and secured within the bell housing forming distal port 106. Sleeve 126 comprises an annular wall 130 comprising an interior surface, which is generally annular, but may be slightly divergently tapered from left to right, as viewed in FIG. 4, to accommodate a press-fit but removable union with a proximal fitting of a tracheal tube, for example, in a manner generally well-known to those skilled in the art. Sleeve 126 also comprises a predetermined length between blunt edges 132 and 134. Edge 132 is radially flush with the outer edge of the bell housing forming distal port 106. Edge 134 rotatably abuts notch 124.

Sleeve 126 also comprises an outwardly directed radially extending retaining flange 136. The location of flange 136 is selected to be adjacent step 118 to accommodate rotation contiguous with the inside of step 118. Sleeve 126 also comprises a relatively thin integral delectably yieldable annular sealing rib or finger 138. Rib 138 extends proximally in an axial direction.

When sleeve 126 is assembled into the position illustrated in FIG. 4, the sealing rib 138 is caused to forcibly engage a surface within the annular slot formed by walls 116 and 122 and be deflected into a firm sealed relation with that surface to thereby hermetically close the interface between sleeve 126 and the bell housing.

Sleeve 126 is retained in the position illustrated in FIG. 4 by an annular rigid plastic collar 140 positioned between walls 116 and 130. Collar 140 is bonded to the surface of wall 116. Thus, collar 140 functions as a bushing with flange 136 and the surface of sleeve 126 contiguously but rotatably engaging the proximal edge and inside annular surface of collar 140.

Sleeve 128, which is rotatably coupled to the bell housing forming proximal port 108, is substantially identical to sleeve 126 being rotatably placed within the bell housing. Sleeve 128 is enumerated identical to sleeve 126 although it will be readily apparent that the sleeve orientation is reversed, the overall length of sleeve 126 is shorter, the sleeve 128 extends beyond the bell housing and the radial flange 136 is positioned closer to the blind slot formed by wails 116 and 122.

Ventilating tubing is compression fit into or over the exposed part of sleeve 128. A tracheal fitting is inserted into the hollow of sleeve 128. Sleeve 128 rotates with any rotation imposed upon the connected ventilating tubing or, alternatively, retain an essentially stationary position if and when the adaptor 104 is rotated, either intentionally or inadvertently in respect to sleeves 126 and 128. Thus, twisting and consequential occluding or partial occluding of ventilating tubing is avoided.

Adaptor 104 further comprises an angularly-disposed proximally-directed barrel, generally designated 142 forming access port 110. Proximally-directed barrel 142 comprises an annular wall, the exterior surface of which is annular, while the interior surface is illustrated as being slightly tapered divergently in a distal direction to receive, in compression-fit relation, an aspirating catheter cartridge, generally designated 34. Cartridge 34 will be explained in greater detail hereinafter.

The interior surface of barrel 142 defines a proximal passageway or access port 110, the diametrical size of which is substantially smaller than either of the two previously described passageways, distal port 106 and proximal port 108. Access port 110 provides a pathway through adaptor 104. It should be noted that the longitudinal axis of distal port 106 and the longitudinal access of access port 110 intersect each other at a relatively small acute angle, which may be on the order of about 20°, to accommodate ease of insertion and centering of a slidable aspirating catheter tube 144, forming part of the aspirating catheter cartridge 34. Catheter tube 144 is flexible along its length to accommodate smooth insertion through a tracheal tube, for example, into either lung of the patient for removal of secretions.

Barrel 142 is preferably formed as one piece with the other components of adaptor 104, excluding swivel sleeves 126 and 128.

Adaptor 104 further comprises a second angularly-disposed proximally-directed barrel, generally designated 146 forming a second access port 112. Barrel 146 comprises an exterior substantially cylindrical surface, and interior surface which is illustrated as being slightly divergently tapered in a distal direction, for purposes yet to be explained. Barrel 146 terminates in a proximal edge, which is blunt and transversely-directed. Barrel 146 comprises a wall of uniform thickness defining access port 112, which merges distally with distal port 106, forming a small acute angle therewith on the order of about 20°, as illustrated in FIG. 4, although other angles could be used. The use of slight acute angles for the access passageways or ports functions to facilely center the distal end of a catheter tube as it is inserted through a given access port. Centering may occur at least in part by acute angle deflection off an interior wall surface of the adaptor or the tracheal tube. Barrel 146 is interrupted by a male transversely directed side port tube 148, the hollow interior of which defines access port 150. The tube 148 comprises a smooth interior annular surface, illustrated as being of uniform diameter and an exterior surface, which is interrupted by an outwardly-projecting radially-directed annular barb, by which a medication-administering attachment, generally designated 66, is secured against inadvertent removal. Barrel 146 comprises part of the one-piece construction of adaptor 104; as illustrated in FIG. 4.

Barrel 146 is illustrated in FIG. 4 as being closed by a tethered, press-fit cap, generally designated 152. Cap 152 is sized and shaped so as to be snugly received in the position illustrated in FIG. 4, somewhat compressively, so that inadvertent removal does not take place.

Cap 152 is formed, as illustrated, of one piece comprising an annular collar, a plug, and a tether, which connects the collar to the plug. The collar of cap 152 is generally annular in its configuration, comprising wall defined by an inside annular surface, the diameter of which is slightly smaller than the diameter of the exterior surface at the proximal end of barrel 146, so that the collar must be force-fit into the position illustrated in FIG. 4 and remains in the illustrated position unless intentionally manually removed.

The plug of cap 152 fits snugly inside a hole in cap 152 to prevent inadvertent removal of the plug. The hole of cap 152 may be substantially smaller than the inside diameter of barrel 146 in order to provide a tight seal against accessory devices placed through access port 112.

By closing the access port 112 with the plug of cap 152, introduction of microbes and other undesired contamination is prevented. Yet, the cap 152 can be quickly and easily manually removed to accommodate introduction through access port 112 of medication, an oxygenation catheter tube, monitoring devices, sampling devices, and visual inspection, instruments, etc.

The attachment 66, connected to side port tube 148, comprises a distal fitting, generally designated 154, which is L-shaped in configuration, as illustrated. One end of distal fitting 154 is force-fit over side port tube 148 and held in place by the barb on tube 148 as illustrated in FIG. 4. The other end of distal fitting 154 is attached to tube 156 either in a compression fit relation, or so as to be bonded or plastic welded in position. Tube 156 may be of any desired length.

Attachment 66 comprises, in addition, a proximal fitting, generally designated 158. Proximal fitting 158 is attached to the proximal end of tube 156, either by force-fit or secured as by plastic welding, bonding, or the like. Proximal fitting 158 may be closed by cap 160 as shown in FIGS. 3 and 4. Cap 160 is preferably sized and shaped so that cap 160 can be manually removed when desired, but will not inadvertently separate from proximal fitting 158. Also as shown in FIGS. 3 and 4 cap 160 may be attached to proximal fitting 158 with a tether.

Proximal fitting 158 may have a cylindrically shaped slit valve, generally designated 162, disposed therein. In cross section, slit valve 162 is generally I-shaped, as seen in FIG. 4, and comprises an end-to-end length substantially equal to the interior length of proximal fitting 158. Slit valve 162 may be formed of silicone rubber, KRATON™, or the like, and comprises an annular wall of uniform thickness throughout, as illustrated, comprising an external surface, an internal surface, as well as blunt transversely disposed distal and proximal edges.

A contoured radially-directed double dome-shaped central wall or diaphragm 164 expands across and normally closes the space within proximal fitting 158. Web or wall or diaphragm 164 is necked down at the annular site where diaphragm 164 joins the wall of slit valve 162, as one piece, making the annular site the weakest part of diaphragm 164, exclusive of one or more central slits. The central slit may be of any desired size so as to be capable of receiving a hollow male end of an instrument therethrough, which may be utilized to serve any number of purposes. For example, respiratory medication may be applied through a hollow male projection physically inserted through the central slit, through which the medication may be dispensed under aerosol pressure or by manual pressure, for example. The central slit is illustrated as being located both at the center of the slit valve 162 and in the region of greatest thickness of diaphragm 164. By providing a centrally thicker wall accompanied by a peripherally weakened wall, the periphery yields more readily allowing somewhat coordinated rotation in the wall at both the periphery and at the central slit when a male projection is physically forced through and removed from the slit both when there is pressure and when there is no pressure at the interior site of the diaphragm 164. Also, the double domed configuration of the diaphragm 164, with the enlarged lips at the slit enhances a return to the normally closed state upon removal of the male projection. As is apparent from the figures fluid introduced through slit valve 162 will enter adaptor 104 through fluid introduction port 150.

Figure 5:
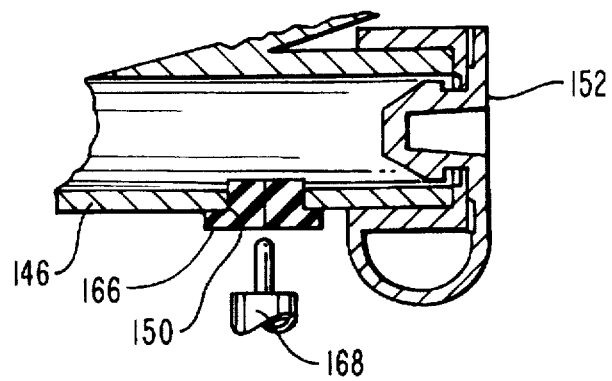
FIG. 5 is a fragmentary cross section of a modified form of the present invention.
Figure 6:
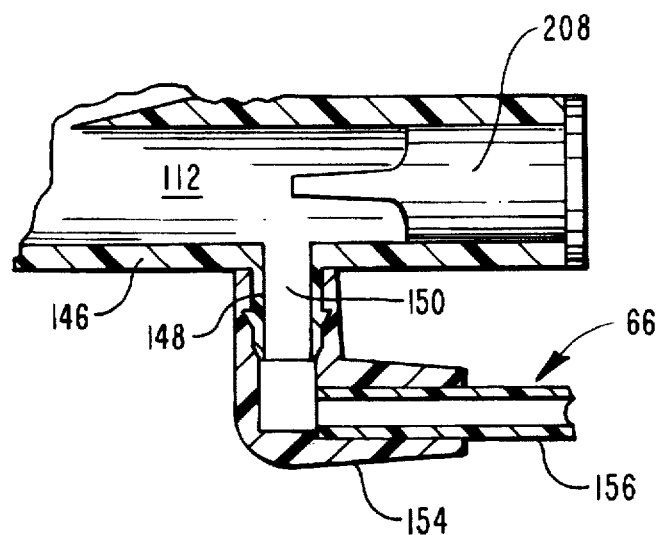
FIG. 6 is an enlarged fragmentary cross section of one access port of one multi-access apparatus.

In lieu of the male side wall tube 156 and attachment 66, a slit valve may be placed directly in barrel 146, as illustrated in FIG. 5. More specifically, the wall of barrel 146 in FIG. 6 is equipped with a liquid introduction port 150 of pre-determined size. A slit valve plug, generally designated 166, sized appropriately, and formed of yieldable synthetic resinous material, is force-fit into port 150 so that the material of slit valve 166, is compressed as illustrated in FIG. 5. Slit valve 166 is illustrated as comprising an enlarged annular flange disposed external of the outside surface of barrel 146, to prevent displacement of the entire slit valve 166 into the interior of barrel 146 when forcibly engaged by hollow male projection of a medication or saline dispenser or container 168.

Referring now to FIGS. 3 and 4, the previously mentioned aspirating catheter cartridge or assembly 34 is described. Catheter cartridge 34 comprises the mentioned aspirating catheter tube 144, illustrated as being of uniform thickness and inside and outside diameter throughout, and a distal fitting 170. Fitting 170 comprises a slightly tapered distally-directed projection 172, shown as being in spaced relation to and telescopic surrounding catheter tube 144, catheter tube 144 being illustrated in FIG. 4 in a withdrawn state. A space or wash chamber 174 exists between the exterior surface of the catheter tube 144 and the interior surface of projection 172. As explained hereafter, the wash chamber allows the exterior of catheter tube 144 to be cleaned or washed. Projection 172 distally merges with an inwardly-directed transverse or radial flange formed as one piece with projection 172. This inwardly-directed annular flange has a central circular opening through which tube 144 contiguously though slidably extends and as shown hereafter limits the passage of wash solution into the respiratory tract of a patient.

Projection 172 has formed therein access port 150, which is aligned with the hollow interior of a transverse, relatively short hollow male projection or tube 178. Tube 178 is formed as one piece with projection 172. Excluding length, hollow tube 178 is constructed substantially identical to the construction of hollow tube 148 and is correspondingly enumerated. No further description is necessary to impart an understanding to one of skill in the art. The hollow tube 178 is connected to a second attachment 66, which is constructed identical to previously described attachment 66 and is so enumerated in FIG. 4.

The attachment 66 of the aspirating catheter cartridge 34 may be used to wash the exterior and interior surfaces of the catheter tube after it is withdrawn from the patient, saline or other suitable wash solution being introduced by a hollow male projection extended through slit valve 162 and thence along the hollow interior of attachment 66 of catheter cartridge 34 through fluid introduction port 176 into wash chamber 174. The inwardly-directed flange at the end of projection 172 limits passing of the wash solution into adaptor 101 and from thence into the respiratory tract of the patient. Used wash solution is evacuated through the hollow of the catheter tube 144 due to suction applied there. Also, lavage may be introduced through attachment 66, in the manner explained above, when the catheter tube 144 is fully or partially inserted into the respiratory tract, which lavage runs slowly down the catheter tube into the respiratory tract.

The distal fitting 170 comprises an annular seal or washer 180 which seals around catheter tube 144. The seal or washer 180 is preferably formed of yieldable synthetic resinous material, such as silicone rubber, and has an inside diameter that compressively engages the exterior surface of the catheter tube 144. Thus, the catheter tube 120 is wiped by seal 180 as it is withdrawn from use in the respiratory system of an intubated medical patient, thereby removing secretions and other materials carried upon the exterior surface of the catheter tube 144 and depositing the same in the wash chamber 174.

Seal 180 is held in place by a double wall collar generally designated 182. Collar 182 has a double flange configuration which provides a certain amount of radially compressibility, which accommodates ready compression fit insertion within the rest of distal fitting 170 with the forward edges of collar 182 holding seal 180 in the illustrated position of FIG. 4. Collar 182 also provides guidance to the catheter tube as it is displaced.

The distal end of a collapsible, preferably transparent, plastic sheath, generally designated 184 is placed over the trailing outside annular surface of collar 182. The end of sheath 184 is held in compression-fit relationship by a ring 186 forced over the end of sheath 184 and collar 182.

Reference is now made to FIG. 3, which illustrates the proximal end of the aspirating catheter cartridge 34. The proximal end of the cartridge 34 comprises seriatim a proximal fitting 188 disposed at the end of the collapsible sleeve or envelope 184, a normally closed valve means such as suction valve 190 and an exteriorally stepped tube, generally designated 192. Fitting 188 is illustrated as being formed as one piece from suitable synthetic resinous material and is secured to suction valve 190 by plastic welding, bonding, or any other suitable fashion.

When the normally closed valve 190 is manually depressed, negative pressure or suction is delivered from a suitable source along a suction tube to the hollow interior of tube 192 across valve 190, through hollow passageways therein, and along the hollow interior of tube 144. When the distal end of the tube 144 is suitably positioned within a selected lung of the patient, secretions accumulated in the lung are auctioned along the hollow interior of the tube 144 through the hollow interior of the control valve 190 and thence through stepped tube 192.

Referring next to FIG. 3, oxygenation catheter cartridge 114 is next described. Oxygenation catheter cartridge 114 comprises a distal fitting 194. With a hollow male projection 196 through which a hollow oxygenation catheter treatment tube 198 can be manually advanced and retracted into and from a suitable lung position for the purpose of oxygenating and potentially replacing residual carbon dioxide within the selected lung with oxygen. The catheter treatment tube 198 is surrounded by a sheath 200 which is similar in structure and function previously described sheath 184. The distal end of the sheath 200 is attached to distal fitting 194.

Oxygenation catheter cartridge 114 comprises a proximal fitting 202 which is attached to the proximal end of the sheath 200. The proximal fitting 202 is centrally hollow and is in fluid communication with the hollow interior of catheter treatment tube 198. After male projection 196 is press-fit into access port 112 and the catheter treatment tube 198 advanced through adaptor 104 into a desired location within the lungs, valve 204 is manually opened, causing oxygen from source 206 to be delivered at a suitable rate and pressure to the selected lung site.

When utilization of the oxygenation cartridge 114 is over (with the catheter tube 198 retracted) cartridge 114 is removed. Another unused oxygenation catheter cartridge of the same or similar construction could be used later when oxygenation is desired. The same approach is true of cartridge 34, i.e., it can be replaced after one or more uses to prevent undesired risks to the patient due to growth of micro-organisms therein with the passage of time. While the configuration of FIGS. 3 and 4 have been described in respect to aspirating and oxygenating catheter assemblies, it is to be understood that the configuration will also accommodate use of other catheter assemblies, such as those used for medication or lavage, or any of the other treatment identified in the summary section of this application including those used to visually inspect selected parts of the respiratory system, to sample sputum and gasses, to sense parameters such as flow rates, pressure and temperature, and/or to flush with washing solution, as well as non-catheter access to the respiratory tract of a patient.

Figure 7:
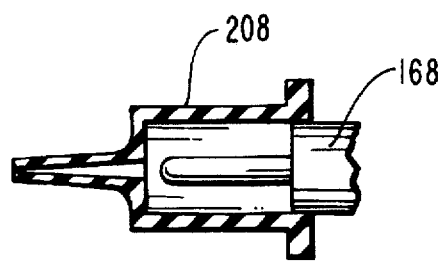
FIG. 7 is a fragmentary cross section of FIG. 6.

Access port 112, can also be utilized to directly receive lavage and/or medication as illustrated in FIGS. 6 and 7, to which reference is now made. In lieu of cap 152 (not forming a part of the embodiment of FIGS. 6 and 7) a one-piece duck bill valve, generally designated 208, is illustrated as being compression-fit into the proximal or trailing end of barrel 146. Duck bill valve 208 is adapted to receive a lavage or medication receptacle 168, a male projection comprising any of the inserted items described in this specification, being illustrated in FIG. 7 as exemplary. The diameter of duck bill valve 208 is slightly greater than the interior of barrel 146. Thus, when inserted duck bill valve 208 remains in place by reason of a radial memory force, outwardly directed, from the duck bill valve 208 against inside of barrel 146. Accordingly, the duck bill valve 208 is made of a suitable synthetic material with memory, which is substantially yieldable.

As can be seen from examination of FIG. 7, valve 208 is formed of one piece from a suitable elastomeric synthetic resinous material, such as silicone rubber. The nature of the construction of valve 208 is such that access port 112 is normally closed by valve 208. However, without removal of valve 208 lavage or medication held in container 168 can be introduced into access port 112 and from thence into the respiratory of the intubated medical patient by causing a hollow male projection of container 168 to be inserted through valve 208. It is to be appreciated that container 168 and its male projection are intended to be illustrative and not restrictive. By way of example only, container 168 can be an aerosol container or a container which can be manually collapsed to discharge the appropriate amount of medication or lavage dose. As illustrated, container 168 is sized so as to be snugly received within the hollow defined by valve 208. Catheters, probes, and other instruments can also be inserted through valve 208 to accommodate samples, monitoring, inspection, and various forms of respiratory therapy as described in the summary section of this application.

Figure 8:
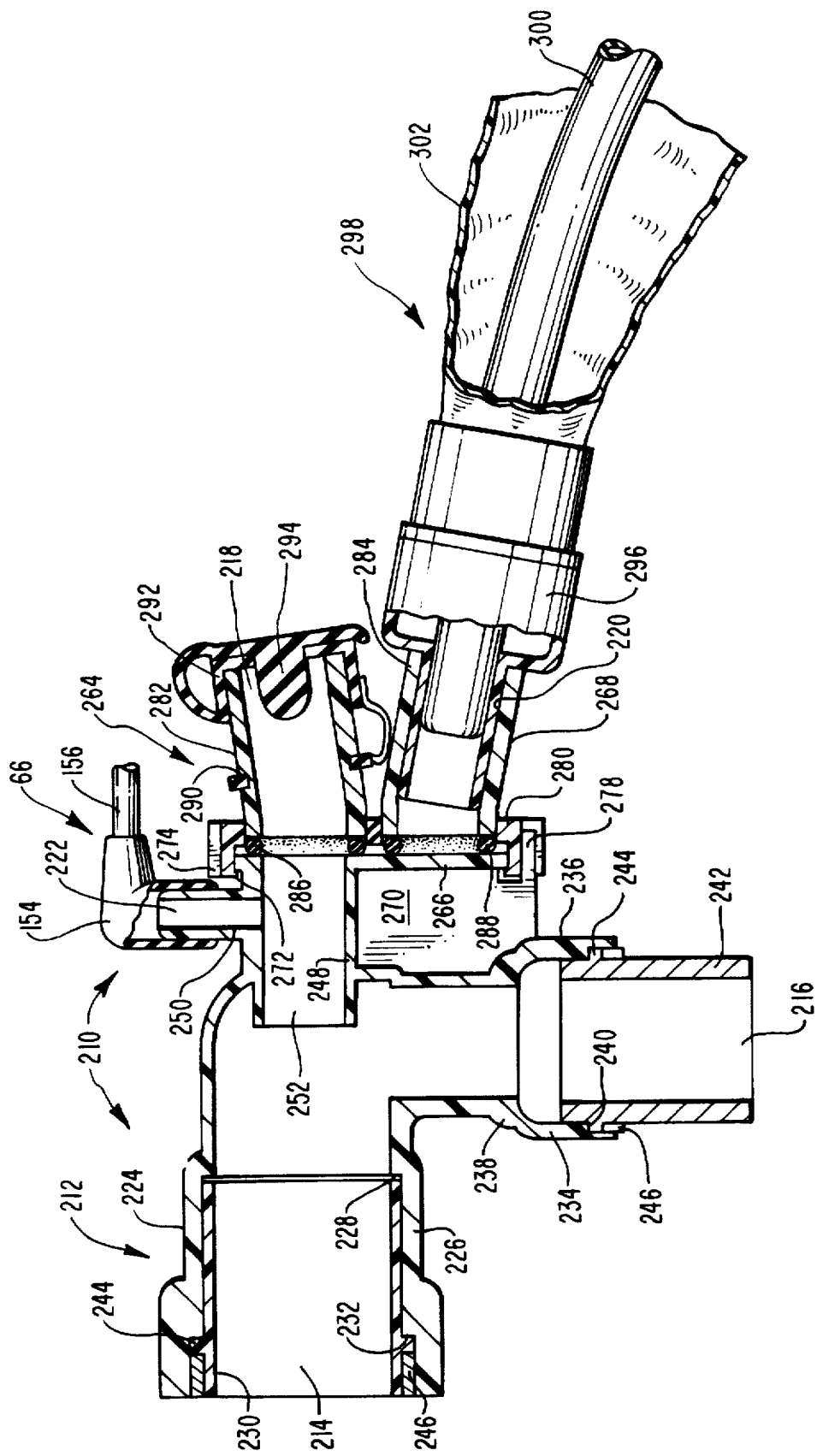
FIG. 8 is a fragmentary exploded perspective of another multi-access apparatus.
Figure 9:
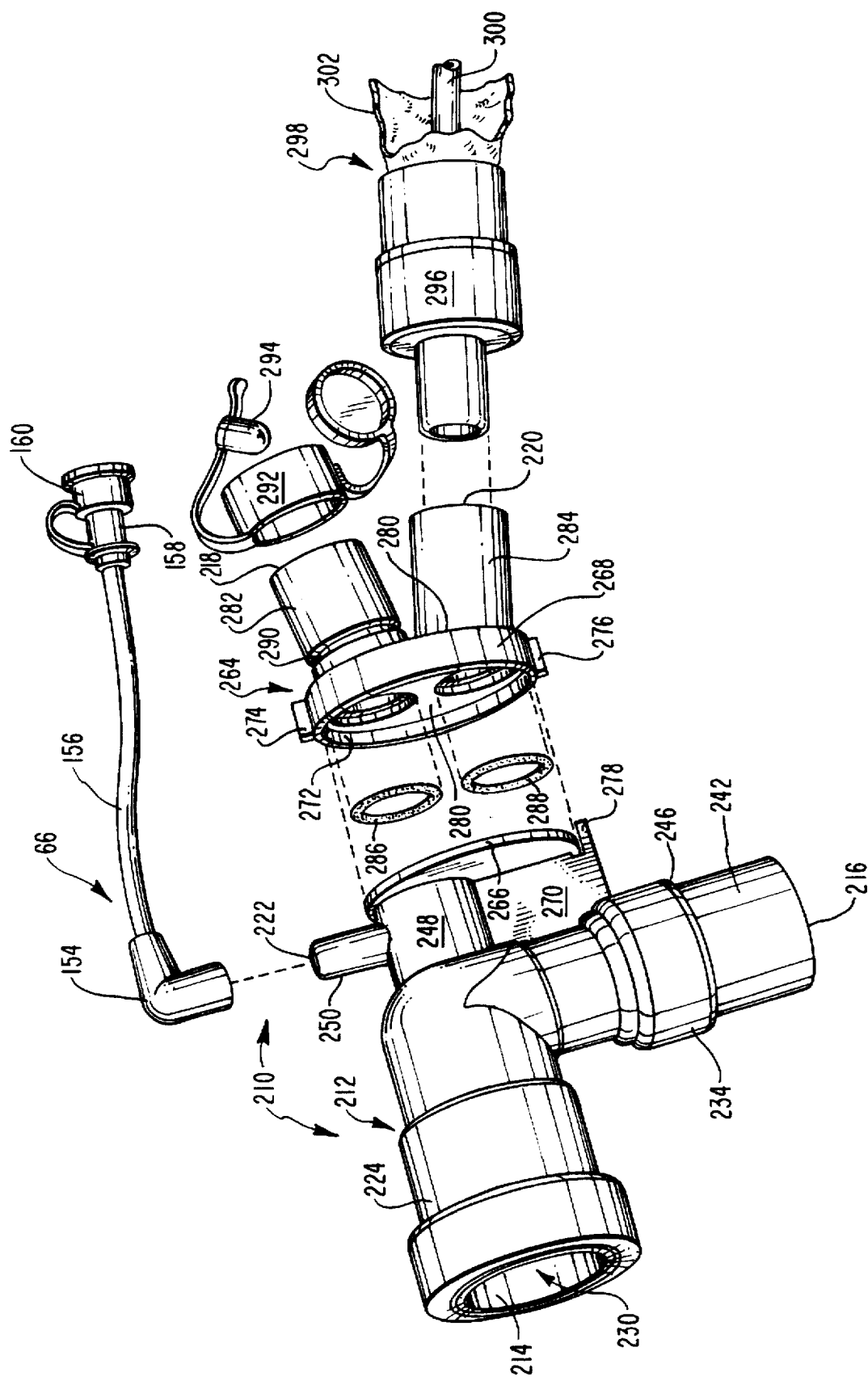
FIG. 9 is a cross section of the device of FIG. 8.

FIGS. 8 and 9 illustrate another multi-access assembly, generally designated 210, for use in conjunction with the respiratory tract of an intubated medical patient ranging from infants to the aged. Assembly 210 comprises an adaptor means for defining a flow path therethrough for delivery of ventilating gasses to an intubated patient and for providing an access path for delivery to the intubated patient such as elbow type connector, manifold, fitting, or adaptor, generally designated 212. Adaptor 212 comprises a distal port 214, a proximal port 216, a plurality of access ports 218, 220 and 222.

For example only, distal port 214 and proximal port 216 accommodate continual cyclic patient ventilation, independent of implementation by the health care provider of any other patient respiratory access procedure. Access port 222 accommodates introduction of irrigation or wash liquid by which the exterior of an aspirating catheter tube, for example, is washed as the catheter tube is withdrawn following use. Port 222 also accommodates delivery of lavage to the interior of adaptor 212. Access ports 218 and 220 accommodate access by an accessory device, such as but not limited to selective insertion and subsequent removal of an aspirating catheter assembly, the catheter tube of which removes secretions from the lungs. Access ports 218 and 220 also accommodate an oxygenation catheter assembly, the catheter tube of which is used in the lungs to replace residual carbon dioxide with oxygen, and/or entry of temperature or pressure monitoring instruments or obtaining samples of sputum or gases and/or to allow insertion of visual inspection instruments. In short, access ports 218 and 220 can accommodate any of the catheter means in this application.

The adaptor 212 comprises a distal tracheal tube bell housing connector, generally designated 224, preferably formed of injection molded rigid medical grade synthetic resinous material, such as acrylic, cryolite, pebax, polypropylene, or the like. Connector 224 comprises a stepped annular wall 226.

Wall 226 comprises a thickness which is variable and stepped, defined by inside and outside surfaces. The distal end of wall 226 is defined by a blunt transverse annular distal edge, where the bell housing 224 comprises its largest outside diameter. Wall 226 comprises a first reduced diameter exterior annular rounded step or shoulder and a second further reduced diameter exterior annular rounded step or shoulder.

Directly adjacent to the second shoulder is an interior shoulder or stop 228, which limits the amount swivel sleeve 230 can be inserted inside bell housing 224. The interior surface of wall 226 comprises an annular shoulder 232, which accommodates rotation of swivel sleeve 230 while preventing axial displacement thereof.

Adaptor 212 also comprises a second bell housing, generally designated 234, in which proximal port 216 is formed and which is constructed to comprise components similar to bell housing 224, although bell housing 234 is substantially shorter in its axial length. Bell housing 234 is illustrated as being disposed at 90° to bell housing 224.

Bell housing 234 comprises an annular wall 236. Wall 236 comprises a thickness which is variable and stepped, defined by inside and outside surfaces. The distal end of wall 236 is defined by a blunt transverse annular distal edge, where the bell housing 236 comprises its largest outside diameter. Wall 236 comprises a reduced diameter exterior annular rounded step or shoulder 238. Shoulder 238 is also interiorly rounded.

The interior surface of wall 236 comprises an annular shoulder 240, which accommodates rotation of swivel sleeve 242, while also limiting the extent to which swivel sleeve 242 is capable of being axially inserted into the bell housing 234.

When fully assembled, sleeve 230 is rotatably positioned and secured within the bell housing 224. Sleeve 230 comprises a generally annular wall comprising an interior surface, which is generally annular, but may be slightly divergently tapered from left to right, as viewed in FIGS. 8 and 9, to accommodate a press-fit but removable union with a proximal fitting of a tracheal tube, for example, in a manner well-known to those skilled in the art. Sleeve 230 also comprises a predetermined length so as to fit flush within bell housing 224.

Sleeve 230 comprises an outwardly-directed radially-extending retaining annular flange or boss 244. The location of flange 244 is selected to be adjacent to step or shoulder 232 to accommodate axial rotation contiguous with shoulder 232.

Sleeve 230 is retained in the position illustrated in FIG. 9 by an annular rigid plastic collar 246. Collar 246 is bonded to the inside surface of wall 226 in the position illustrated in FIG. 9. Thus, collar 246 functions as a stationary bushing with flange 244 of sleeve 230 to contiguously but rotatably engaging the inside edge surface and inside annular surface of collar 246.

Sleeve 242, which is rotatably coupled to bell housing 234, is substantially similar to sleeve 230, being rotatably placed within bell housing 234. Sleeve 242 is enumerated identical to sleeve 230, although it will be readily apparent that the sleeve orientation is reversed, the thickness of sleeve 230 is less than the thickness of the sleeve 242, sleeve 242 extends beyond bell housing 234 and the radial flange 244 is positioned closer to the edge of sleeve 242.

Ventilating tubing is conventionally compression fit over the exposed surface of sleeve 242. A tracheal fitting, as stated above, is inserted into the hollow interior of sleeve 230, to complete the ventilating circuit. Sleeve 242 rotates with any rotation imposed upon the connected ventilating tubing or, alternatively, retain an essentially stationary position if and when the adaptor 212 is rotated, either intentionally or inadvertently, in respect to sleeves 230 and 242. Thus, twisting and consequential occluding or partial occluding of ventilating tubing is avoided.

The bell housings 224 and 234 integrally merge with an L-shaped segment, to provide an L-shaped passageway through the adaptor 212. The L-shaped segment, merges into two cylindrical wall segments 248 and 250, which respectively define proximal access pathway 252 and access port 222.

Pathway 252 is sized and shaped so as to accommodate access by any of the previously mentioned accessory devices. Port 222 accommodates selective passage of irrigating liquid and/or lavage. Wall 250 is annular, diametrally relatively small and centrally hollow. Wall 250 receives, in force-fit relation, one leg of an L-shaped elbow of an irrigation or lavage delivery system, generally designated 66. System 66 comprises a hollow tube 156 which extends into and is secured within a leg of elbow 154, a proximal fitting 158, a proximal cap 160, and a tether securing the cap against loss when it is disconnected from fitting 158.

As illustrated in FIG. 9, the hollow interior of wall 248 is unobstructed and diametrically smaller than the diameter of either port 214 or port 216, but larger than port 222, port 216 being diametrally smaller than port 214.

The assembly 210 comprises access control means such as a turret valve, generally designated 264. Turret valve 264 comprises a stator, generally designated 266, and a rotor, generally designated 268.

The stator 266 comprises a flat stationary plate, which is formed as one piece with both a support flange 270 and wall 248. The intersection between wall 248 and the flat plate defines the proximal opening of pathway 252.

The rotor 268 comprises an annular inwardly-directed radial lip 272, which is force-fit over and is selectively rotatable in respect to stator plate 266 to create the assembly illustrated in FIGS. 8 and 9. The relationship between the peripheral edge of the stator and the lip 272 comprises a guide, track or cam/cam follower. Thus, when assembled, the rotor 268 can be manually turned in respect to the stationary stator plate 266, to an extent and for purposes yet to be explained. The rotation is limited, in the illustrated embodiment, to approximately 180°. More specifically, the rotor 268 comprises means to limit the rotation of the turret valve such as outwardly-extending stops 274 and 276 which are sized, shaped, and positioned so as to have a diameter which will cause engagement with stop cantilevered finger 278 of stator 266 when rotor 264 is rotated. Thus, the stop 278 allows but limits rotation of the rotor 264 until either stop 274 or stop 276 makes contact therewith. Accordingly, when viewed from the right in FIG. 8, clockwise rotation of the rotor 264 will bring the stop 276 into contact with stop finger 278, whereas counter-clockwise rotation of the rotor 264 will bring the stop 274 into contiguous contact with stop finger 278.

The rotor base plate 280 comprises two apertures formed therein and two tubes 282 and 284 sized and shaped so that the distal ends thereof fit snugly into and are permanently secured therein by any suitable technique. While tubes 282 and 284 are shown as being initially formed separate from the rotor base 280, they could be formed as one piece with rotor base 282 using conventional injection molding techniques. Tubes 282 and 284 define access port 218 and 220, respectively.

A pair of O-rings 286 and 288 are compressively positioned between the distal end of tubes 282 and 284 and the stator base plate so as to prevent leakage at that location. The O-rings 286 and 288 have a diametral size slightly greater than the diametral size of pathway 252 and the diametral size of access ports 218 and 220. Thus, when the rotor 268 is positioned as illustrated in FIG. 8, access port 218, the hollow center of O-ring 286, and pathway 252 are substantially aligned.

Tubes 282 and 284 may be slightly angular one to another, to prevent interference. Tube 282 also comprises an external annular groove 290 into which a radially stretched tether ring of cap 292 is placed and thereafter contracted so that the tether ring, in the assembled position, exerts a compressive force upon the base of groove 290. Cap 292 comprises a central aperture that can be closed by plug 294 which has a diameter that is slightly greater than the diameter of the central aperture so that full insertion of plug 294 into the central aperture diametrally enlarges or stretches the aperture to create a compression-fit, sealed relation. Plug 294 can be manually pulled or pried from the central aperture, to accommodate subsequent insertion of an accessory device through the aperture. A tether prevents misplacement of the plug 294.

Cap 292 can also be manually removed from the position illustrated in FIG. 9 at the proximal end of tube 282, to accommodate placement of any desired accessory device directly into access port 218, without passage through the smaller central aperture of cap 292. When cap 292 has been so removed, the tether ring in groove 290 prevents loss of either or both the cap 292 and the plug 294.

It is to be appreciated that rotor 264 is selectively manually rotated from the position of FIG. 8 to a position about 180° out of phase with the position of FIG. 8, where tube 282 is located out of alignment with pathway 252 and tube 284 is in alignment with pathway 252. As this rotational displacement occurs, O-ring 286, at its distal contact with the flat stator plate simply sealingly slides therealong from the aligned to the non-aligned position.

It is also possible for the user to rotate rotor 264 so that neither tube 282 nor tube 284 is aligned with pathway 252. During any of the non-aligned conditions, O-rings 286 and 288 and flange 272 do not allow entry of contamination, nor escape of ventilating gases, nor loss of pressure from within the interior of adaptor 212.

Tubes 282 and 284 define access ports 218 and 220, into which the distal end of certain accessory devices can be inserted. As disclosed in the summary, these accessory devices or catheter means are used to aspirate secretions from the lungs and provide other treatment such as to oxygenate the lungs to eliminate or reduce residual $CO_2$ therefrom, to visually inspect selected parts of the respiratory system, to sample sputum and gasses, to sense parameters such as flow rates, pressure, and temperature, to flush with washing solution, and/or administer medication, gasses, and/or lavage. More specifically in reference to FIG. 8, a distal fitting 296 is illustrated as being press-fit into access port 220. The press-fit relationship can be manually overcome when desired. Distal fitting 296 is illustrated as being part of an aspirating catheter assembly, generally designated 298, which also comprises an aspirating catheter tube 300 around which a collapsible sheath or envelope 302 is positioned.

When access port 220 is aligned with pathway 252, in the manner explained above, the health care provider can thereafter conventionally insert catheter tube 300 into the respiratory tract of the patient to remove secretions and the like in a well-known fashion. While aspirating catheter assembly 298 is illustrated as being an accessory device positioned in tube 284, it is to be appreciated that accessory devices other than an aspirating catheter assembly can be used in conjunction with access port 220.

Aspirating catheter cartridge 298 is similar to aspirating catheter cartridges previously described except that catheter cartridge 298 does not have a lavage assembly. Since the embodiments illustrated in FIGS. 8 and 9 have lavage assembly 66 attached to adaptor 212, the individual accessory devices do not need to have individual lavage assemblies. Other than this difference, construction and operation of catheter cartridge 298 is similar to other aspirating catheter cartridges previously described.

Figure 10:
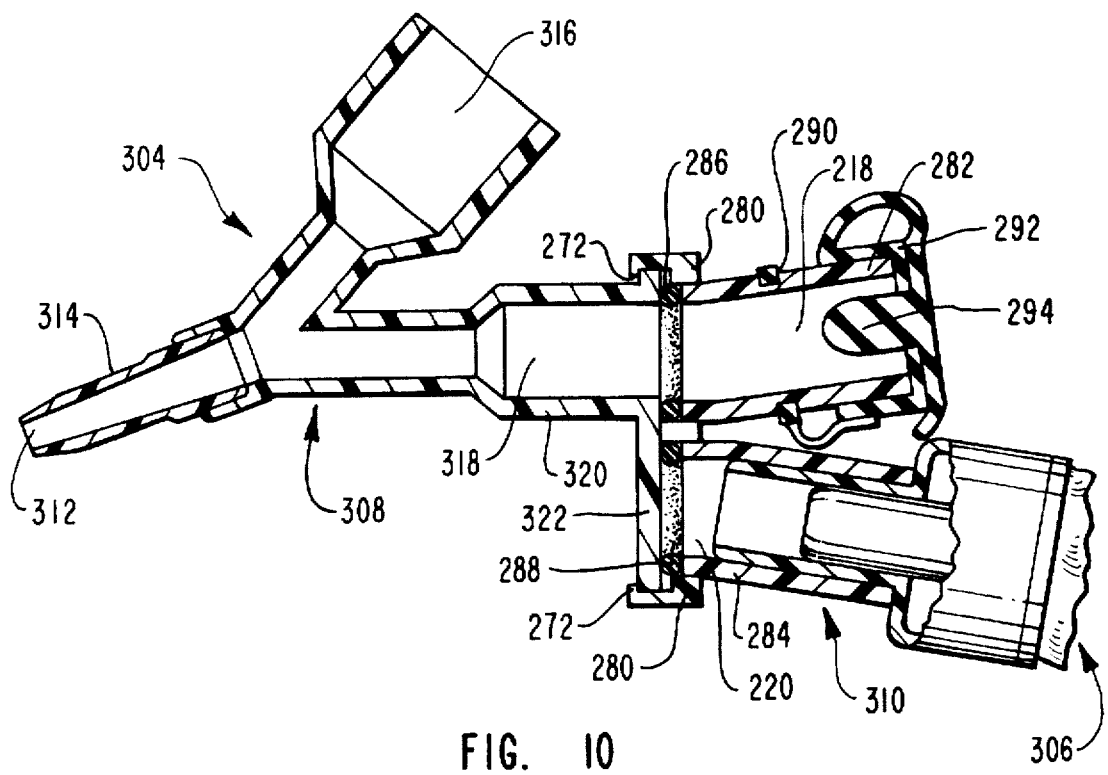
FIG. 10 is a fragmentary cross section of another configuration.

Reference is now made to FIG. 10, which illustrates an additional multi-access respiratory apparatus, generally designated 304, embodying principles of the present invention. Apparatus 304 comprises an accessory device 306, a Y-adaptor, generally designated 308, comprising access control means such as turret assembly 310.

Adaptor 308 comprises a distal port 312 defined by distal hollow tubular tip member 314, adapted to be force-fit into a port-defining opening in a tracheal fitting or into a fitting-less exposed proximal end of an indwelling tracheal tube, which also accommodates patient ventilation. The tip 314 is tapered at its end to accommodate such insertion, while its exterior cylindrical wall surface accommodates a compression fit. Adaptor 308 also comprises a proximal port 316 adapted to accommodate introduction and exhaustion of ventilating gases. The access passage 318 defined by wall 320 is adapted to accommodate access to the interior of Y-adaptor 308 by any one of several accessory devices such as device 306. Thus, the interior surface of enlarged cylindrical or annular wall 320, is illustrated as sized to accommodate access of an accessory device. Barrel 320 merges as one piece with a stator plate 322 forming a part of access control device 310. Stator plate 322 is substantially identical to previously described stator plate 266 of FIGS. 8 and 9. Control device 310 is substantially identical to previously described turret valve 264 of FIGS. 8 and 9, except stops 274 and 276 have been eliminated. The components of control device 3210 have otherwise been enumerated identical to the above-described components of valve 264 of FIGS. 8 and 9 to indicate identity or substantial identity and no further description of these components is required for those skilled in the art.

Figure 11:
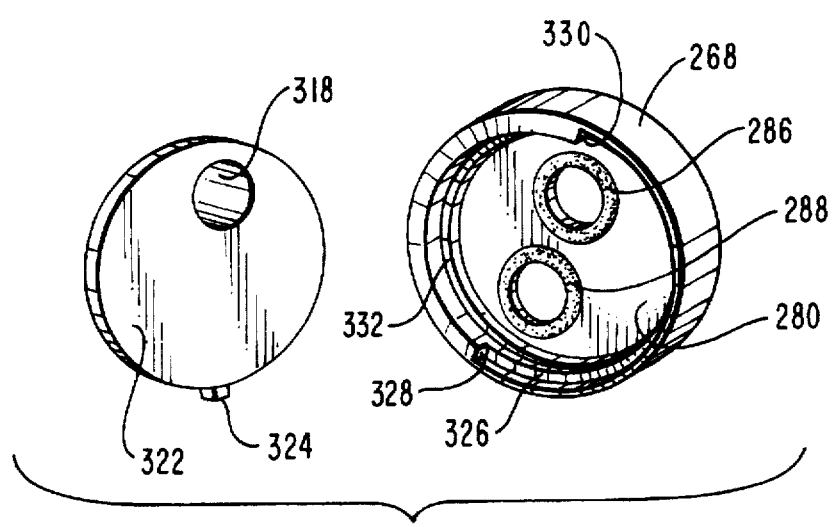
FIG. 11 is an enlarged exploded perspective of a rotor valve embodying principles of the present invention.

In lieu of stops 278,274 and 276 of turret valve 264 of FIGS. 8 and 9, the means for limiting rotation in embodiment of FIG. 10 preferably uses stops internally located within the control device 322. The internal stops depicted in FIG. 11 are suitable. More specifically, as illustrated therein, stator plate 322 may comprise a male edge stop projection 324, which is eccentric to the plate 322 and is placed in a female 180° slot or groove 326 of the flange of the rotor 268. Each end of the groove 326 comprises a blunt abutment surface or stop shoulder 328 and 330. Either stop 328 or 330 can, by rotation of rotor 268 be placed contiguous with the male stop 324 to align the interior of either tube 282 or tube 284 with the passageway 318. The peripheral edge of plate 322 is snap-fit into blind guide groove 332, to provide aligned rotor rotation.

Figure 12:
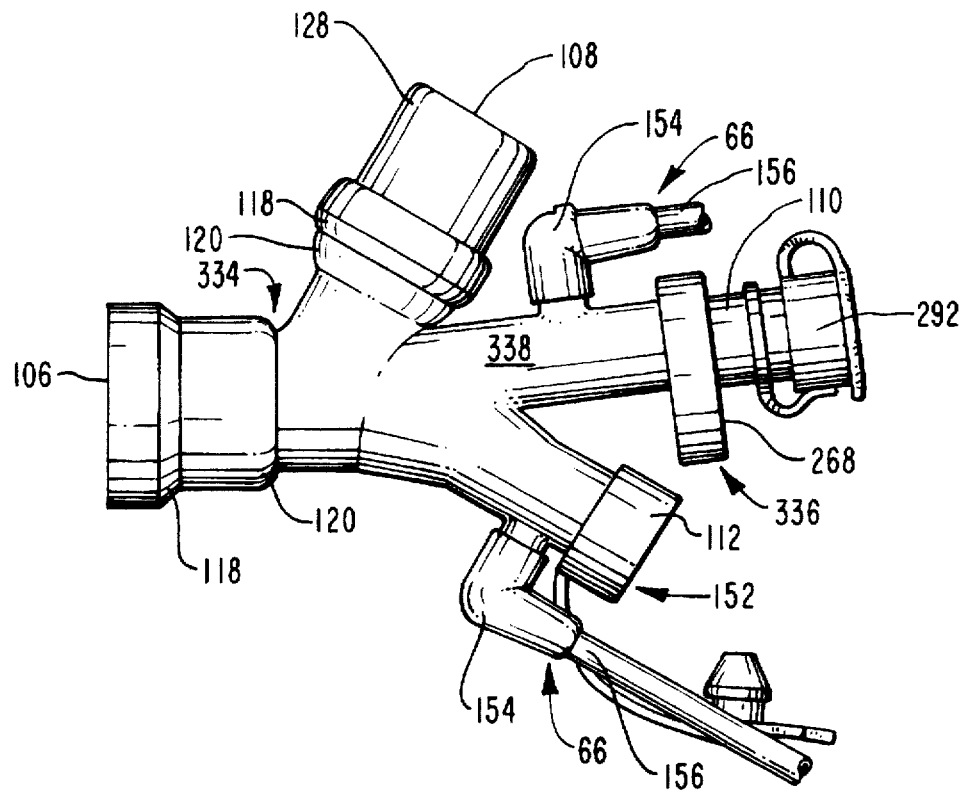
FIG. 12 is a side elevation of another multi-access device.
Figure 13:
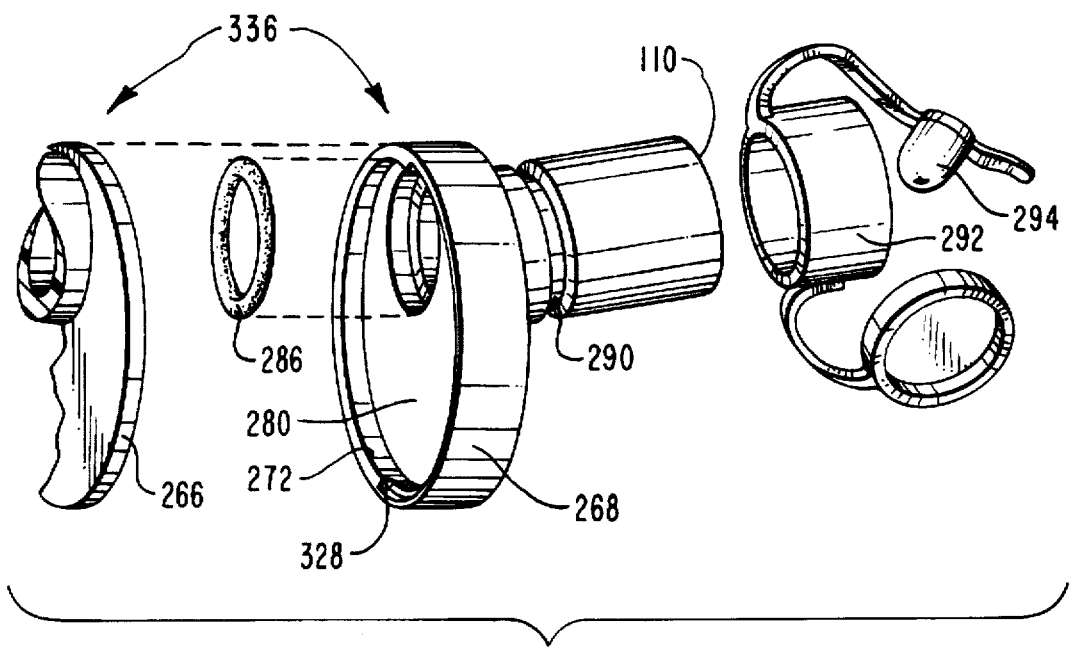
FIG. 13 is a partial exploded perspective of the device of FIG. 12.

Reference is now made to FIGS. 12 and 13, which illustrate a further multi-access manifold, fitting, or adaptor, generally designated 334 comprising access control means such as access control device 336, which is in the nature of a turret valve having only one passageway through the rotor thereof for alignment and misalignment of a proximal access port of the manifold 334 to accommodate access to the interior of the manifold 334 by an accessory device through the control device 336.

Adaptor 334 is substantially the same as adaptor 104 of FIGS. 3 and 4 with the exception that access port 110 is capped by cap 292, adaptor 334 has access control means for providing selective access through the adaptor, such as access control device 336, and adaptor 334 has been modified to include a lavage delivery system 66.

Control device 336 comprises a turret valve, certain components of which are the same, and so numbered in FIGS. 12 and 13, as previously described in respect to turret valve 264, except as otherwise specified herein. O-ring 288, tube 284, and the external stops 274, 276 and 278 have been eliminated. Internal stops 328 and 330 are used. Thus, turret valve 336 provides only a single or registered enabled position, i.e., where port 110 thereof is substantially aligned with barrel 338, which provides a pathway for accessory devices.

Barrel 338 is illustrated as being equipped with the previously described lavage/irrigation delivery system 66.

Figure 14:
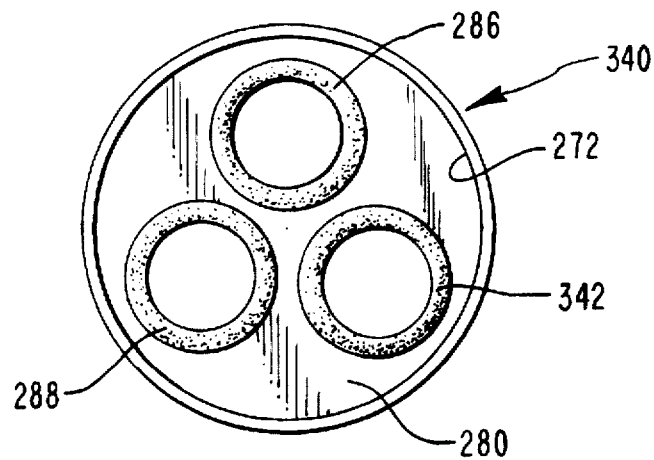
FIG. 14 is a frontal elevation of still another turret configuration.

The present invention embraces use of access control means such as a control device in conjunction with a connector, manifold, fitting and/or adaptor in which the control device is not limited to one or two selective repositionable passageways. For example, three such passageways may be used as is illustrated in FIG. 14. FIG. 14 depicts only a rotor portion, generally designated 340, of a turret valve control device, which also comprises a stator plate of the type heretofore described. Rotor 340 comprises the previously described plate or base plate 280 and lip 272. Plate 280 of FIG. 14 comprises three ports or passageways around which O-ring seals 286, 288, and 342 are respectively compressively situated for the same purpose described above.

By manually rotating rotor 340 in respect to its associated stationary stator plate, any desired one of the three access ports can be enabled or placed in registry with an access path of an associated connector, fitting, manifold or adaptor, while at the same time the other two access ports are disabled. Any such enabled access port accommodates communication into the manifold, fitting or adaptor by a desired accessory device. Any access port in a disabled or non-registered position can accommodate attachment and detachment of a desired accessory device at that site.

Figure 15:
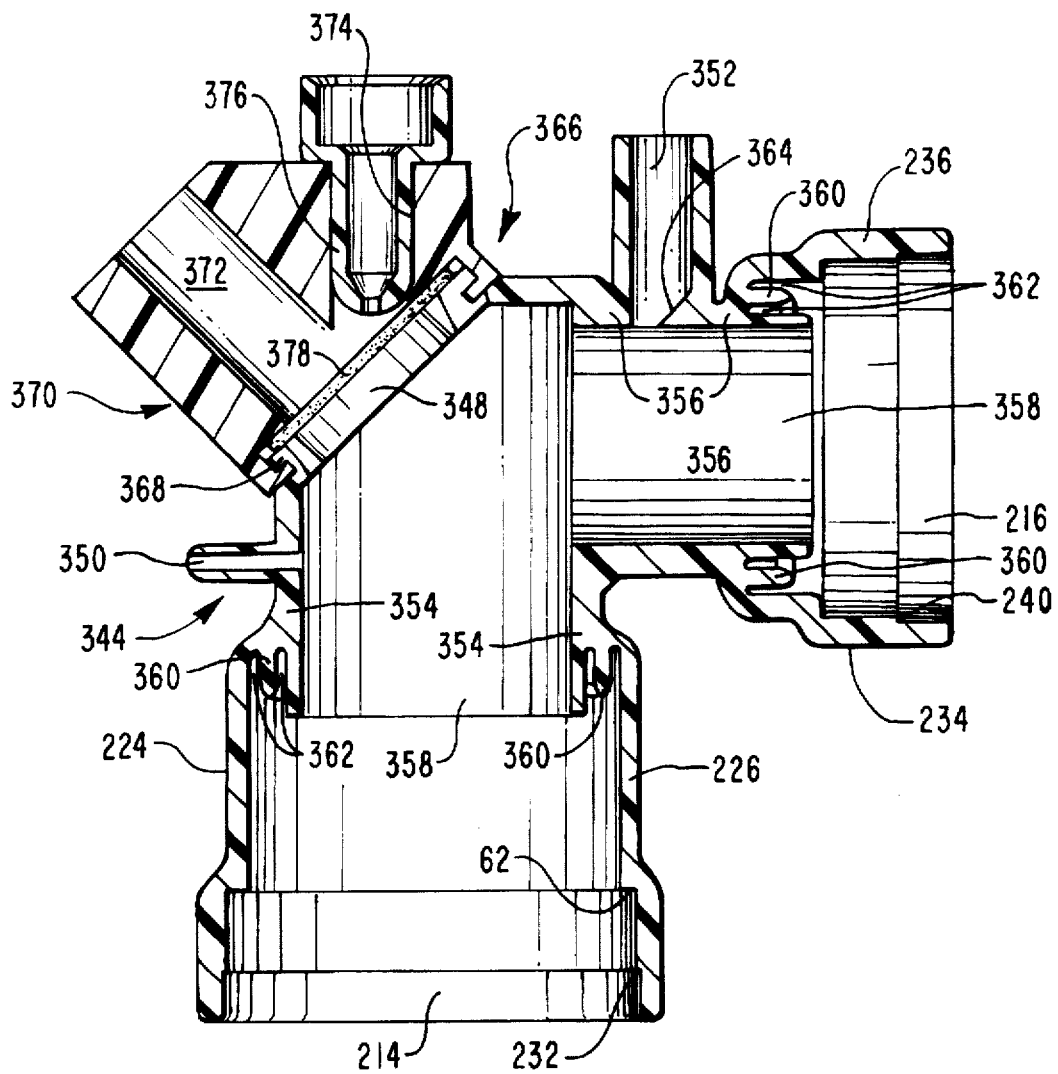
FIG. 15 is a cross section of still another configuration of a multi-access device.
Figure 16:
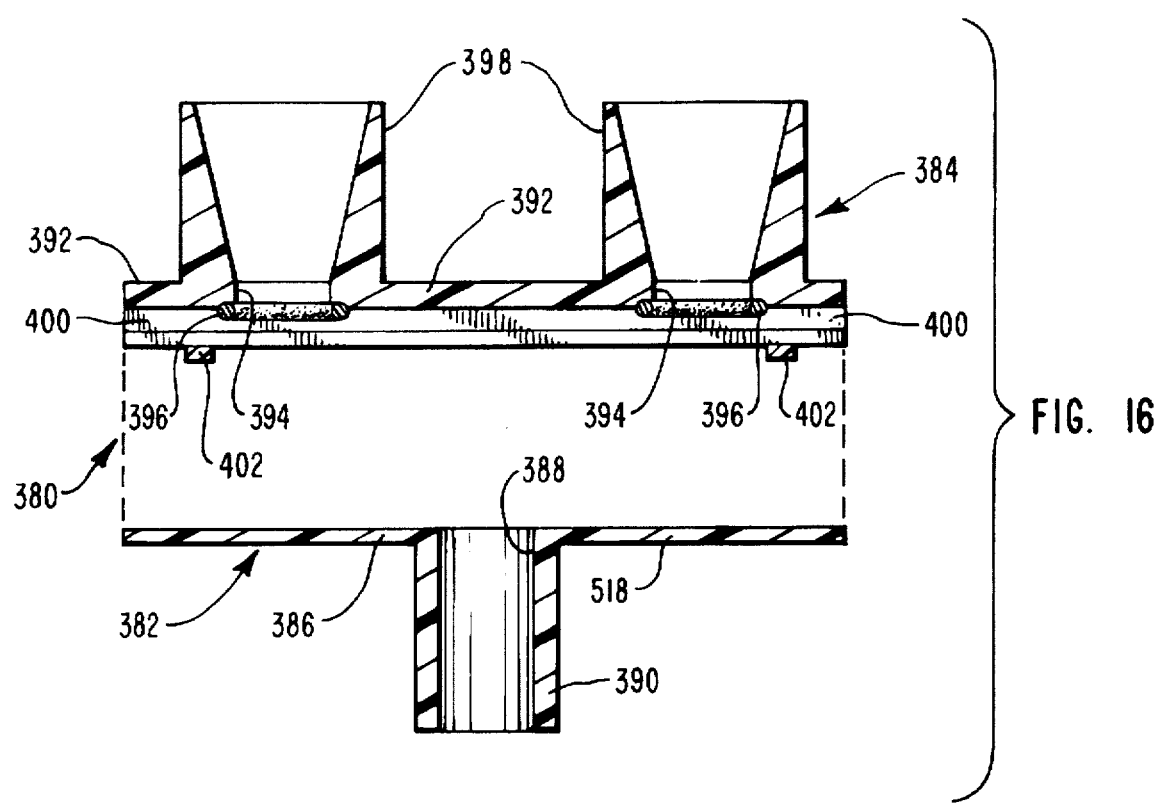
FIG. 16 is a cross section of a slider valve embodying the principles of the present invention.

Reference is now made to FIG. 15 which illustrates a further manifold, generally designated 344, which is in the form of an elbow fitting. The features and components of elbow 344 duplicate a substantial number of the features and components of previously described elbow 212 to the extent FIG. 15 is correspondingly enumerated.

Elbow 344 differs from elbow 212 in the ways described below. Tubes 282 and 284 have been replaced by access ports 372 and 374 formed in rotor 370, access pathway 252 has been replaced by port 348, and access port 222 has been replaced by access port 350. Swivel sleeves for ports 214 and 216 are not shown for ease of illustration and description.

The hollow L-shaped corner of adaptor 344 is defined primarily by two generally cylindrical or annular walls 354 and 356. Walls 354 and 356 each comprise an annular segment 358 which cantilevers into ports 214 and 216, respectively. A longitudinally-directed cantilevered ring 360 is disposed in concentric relationship between wall 226 and the adjacent segment 358 and between wall 236 and the adjacent segment 358. Thus, two spaced parallel annular blind grooves 362 are formed on opposite sides of each ring 360. These blind grooves 362 are designed to receive spaced sealing elements of a swivel sleeve when inserted into each of ports 214 and 216, respectively.

Adaptor 344 has been provided with a further medication port 352. Medication port 352 opens into the hollow interior of the adaptor 430, adjacent to diagonal baffle 364, by which medication delivered to port 352 is deflected toward the hollow interior of adaptor 344 toward the corner to enhance delivery, in an atomized form, to the patient, using ventilating gases as a carrier.

Figure 17:
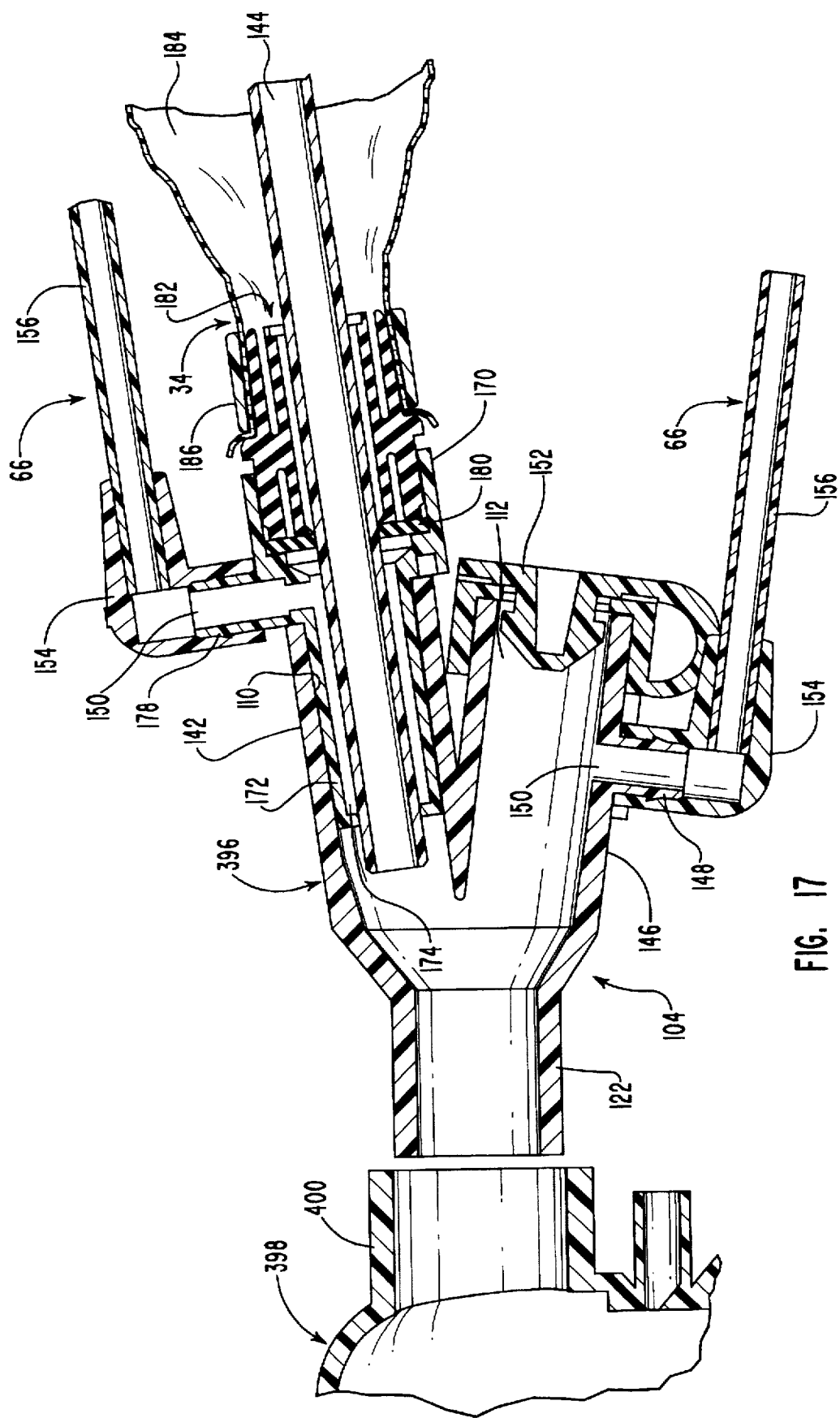
FIG. 17 is a cross section of an additional multi-adapter embodiment of the invention.

Lavage and/or irrigation liquid can selectively be delivered through port 350, for example, in the manner described above. Where port 352 is used for medication, use of port 350 can be limited to irrigation, if desired.

Adaptor 344 comprises access control means such as access control device 366. Access control device 366 comprises stator flange 368. In addition to stator flange 368, control device 366 comprises a rotor, generally designated 370. Rotor 370 comprises a body of material which defines angularly disposed access ports 372 and 374. By manually rotating rotor 370, either port 372 or port 374 is principally placed in registry with distal port 214. The registry position of port 374 is shown in FIG. 15.

An accessory device can be received at either or both access ports 372 and 374, a distal fitting 376 of an accessory device being illustrated in FIG. 15 as compression-fit into port 374, for illustrative purposes. Either or both ports 372 and 374 can be temporarily plugged, capped, or closed in any suitable way, such as is explained above.

O-ring 378 is compressively interposed between stator flange 368 and rotor 370 slightly beyond the diametral limits of port 348. The O-ring seal 378 accommodates rotation of rotor 370 to align either port 372 or port 374 with distal port 214, while preserving its sealing relation.

Reference is now made to FIG. 16 that illustrates a further embodiment of an access control device, generally designated 380, which is yet another example of access control means. Access control device 380 comprises a slider valve by which any one of a plurality of access ports can be enable& i.e., aligned or placed in registry with a single access pathway. Slider valve 380 comprises stator element, generally designated 382, and slider element, generally designated 384.

Stator 382 comprises a flat elongated plate 386, illustrated as being of uniform thickness throughout. Plate 386 comprises two parallel side edges along which the slider element slides back and forth. Single port stator plate 386 is centrally interrupted by a single circular aperture 3880 Plate 386 merges as one piece with a distal cantilever tube 390, the cylindrical hollow interior of which is aligned with and of the same diametral size as aperture 388. Tube 390 is adapted to be compression-fit to a proximal access port of a connector, manifold, fitting, or adaptor.

Dual port slider 384 comprises a flat rectangular plate 392, which comprises two parallel edges that slide along the parallel edges of stator plate 386. Plate 392 is illustrated as being of uniform thickness. Spaced openings 394 exist through plate 392. A rounded seat is provided in the surface of plate 392 around each opening 394 to receive an O-rings 396.

A cylinder 398 surrounds each opening 394. The tapered interiors of the cylinders 398 accommodate compression-fit insertion and removal of a distal fitting of an accessory device. Cylinders 398 can be closed, capped, plugged, or the like when not in use.

The plate 392 merges as one piece, top and bottom, with a channel-shaped edge 400 connected to the top of the plate, at a 90° angle thereto. Channel-shaped edge 400 forms a U-shaped groove. The width of the groove is just slightly greater than the thickness of plate 386 so that when plate 386 is placed within the groove slider 384 can be displaced back and forth within the groove, which serve as tracks or guides for such displacement.

When assembled, each O-ring 396 is compressed between the associated seat and plate 386 to seal the associated port 394. Both O-rings 396 slide back and forth with slider 384, while retaining their respective sealed relation between their respective seats and plate 386.

A pair of bars 402 if desired, can be integrally connected to slider 384 and span underneath plate 386 of stator 382 at spaced locations such that contact between one bar 402 and the tube 390 will align one access port 394 with port 388, while contact between the other bar 402 and the tube 390 will align the other access port 394 with port 388. Thus, either access port 394 can be enabled or placed in registry for communication of an accessory device to the interior of an associated manifold, for example, via aligned access ports 394 and 388. The non-aligned access port 394 is disabled, allowing for attachment and/or detachment of a selected accessory device at the disabled access port 394.

Reference is now made to FIG. 17 which illustrates an additional mariner in which the number of access ports available to the respiratory tract of an intubated medical patient can be enlarged through use in tandem of an elbow and a multiple port Y adaptor generally designated 396. More specifically, the multiple access apparatus of FIG. 17 is illustrated as comprising an elbow adaptor 398 and the second adaptor 396, which comprises an adaptation of adaptor 104 illustrated in FIGS. 3 and 4 and described earlier. Elbow adaptor 398 forms a removable coupling to the tracheal tube of an intubated patient and is more fully described in copending application Ser. No. 08/591,950 previously incorporated by reference. Also illustrated in copending application Ser. No. 08/591,950 are other adaptors which form a removable coupling to the tracheal tube of an intubated patient and which can also be used in conjunction with Y adaptor 396.

Adaptor 396 eliminates the proximal swivel connector, replacing it with the solid wall closing proximal port 108 and also eliminates the distal swivel connector. Otherwise, adaptor 396 is constructed and functions as heretofore described in respect to adaptor 104 and is so enumerated in FIG. 17.

No further description is necessary, other than to point out that ventilation occurs in the apparatus of FIG. 17 through elbow adapter 398, making elimination of the swivel connectors feasible and advisable.

Cylindrical wall 122 is sized and constructed so as to comprise a distal edge and to present a diameter which accommodates a press-fit union against the interior surface of cylindrical wall 400. Accordingly, the single proximal access port defined by cylindrical wall 400 is, in effect, increased two-fold by utilization of adapter 396, which provides access ports 110 and 112 as explained earlier.

The invention may be embodied in other specific forms without departing from the spirit of essential characteristics thereof. The present embodiments therefore to be considered in all respects as illustrative and are not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. An adapter assembly for connection to a proximal end of an endotracheal tube and to a ventilator so as to provide ventilation of an intubated patient's respiratory tract, and for delivering respiratory therapy by way of aspiration of fluids and by way of other treatment including any one of delivery of fluids, removing patient samples or providing visual inspection of the respiratory tract through the endotracheal tube without interruption of ventilation, said adapter assembly comprising:

adapter means for providing a flow path therethrough which is substantially axially aligned with and adapted for fluid communication with a proximal end of an endotracheal tube, said adapter means comprising a distal port means adapted for removable coupling to a proximal end of an endotracheal tube, proximal port means adapted for removable coupling to a ventilator, first access port means for providing a substantially axially aligned access to said flow path by a first catheter means for aspirating a respiratory tract, and second access port means for providing a substantially axially aligned access to said flow path by a second catheter means adapted for providing said other treatment;

an access control means for selectively positioning one or the other of said first and second access port means in substantial axial alignment with said flow path;

first catheter means, connected to said first access port means, for aspirating a respiratory tract when desired, said first catheter means being slidably positionable through said first access port means for substantially axially aligned entry through said flow path and into a proximal end of an endotracheal tube; and second catheter means, connected to said second access port means, for providing said other treatment when desired, said second catheter means being slidably positionable through said second access port means for substantially axially aligned entry through said flow path and into a proximal end of an endotracheal tube.

2. An adapter assembly as defined in claim 1 wherein said access control means comprises a stator means having an opening therethrough that is in substantial axial alignment with said flow path, and rotor means having said first and second access port means mounted thereon, said rotor means being rotatable to a first position wherein said first access port means is in fluid communication and is aligned with said stator opening and said second access port means is not in fluid communication and is not in alignment with said stator opening, and said rotor means being rotatable to a second position wherein said second access port means is in fluid communication and is aligned with said stator opening and said first access port means is not in fluid communication and is not in alignment with said stator opening.

3. An adapter assembly as defined in claim 2 wherein said rotor means is rotatable to a third position wherein neither of said first and second access port means are in fluid communication and are not in alignment with said stator opening.

4. An adapter assembly as defined in claim 1 wherein said first catheter means comprises a distal end permanently connected to said first access port means.

5. An adapter assembly as defined in claim 1 wherein said first catheter means comprises a distal end removably connected to said first access port means.

6. An adapter assembly as defined in claim 1 wherein said second catheter means comprises a distal end permanently connected to said second access port means.

7. An adapter assembly as defined in claim 1 wherein said second catheter means comprises a distal end removably connected to said second access port means.

8. An adapter assembly as defined in claim 1 further comprising third access port means, positioned adjacent one of the first and second access port means and essentially normal thereto, for providing introduction of a lavage fluid in conjunction with said one of the first and second access port means.

9. An adapter assembly as defined in claim 8 further comprising fourth access port means, positioned adjacent the other of said first and second access port means and essentially normal thereto, for providing introduction of a lavage fluid in conjunction with said other of the first and second access port means.

10. An adapter assembly as defined in claim 1 further comprising third access port means, positioned adjacent either one of the first and second access port means and essentially normal thereto when said one or the other of said first and second access port means is positioned in substantial axial alignment with said flow path, for providing introduction of a lavage fluid in conjunction with said either one of the first and second access port means.

11. An adapter assembly as defined in claim 1 wherein said adapter means comprises a first adapter having a distal port for releasable connection to a proximal end of an endotracheal tube, and a proximal port, and further comprising a second adapter having a distal end with means for releasable coupling to the proximal port of the first adapter, and wherein the proximal port means adapted for removable coupling to a ventilator and the first and second access port means are each formed as part of the second adapter.

12. An adapter assembly for connection to a proximal end of an endotracheal tube and to a ventilator so as to provide ventilation of an intubated patient's respiratory tract, and for delivering respiratory therapy by way of aspiration of fluids and by way of other treatment including any one of delivery of fluids, removing patient samples or providing visual inspection of the respiratory tract through the endotracheal tube without interruption of ventilation, said adapter assembly comprising:

adapter means for providing a flow path therethrough which is substantially axially aligned with and adapted for fluid communication with a proximal end of an endotracheal tube, said adapter means comprising:

a distal port means adapted for removable coupling to a proximal end of an endotracheal tube;

23 proximal port means adapted for removable coupling to a ventilator;

first access port means for providing a substantially axially aligned access to said flow path by a first catheter means for aspirating a respiratory tract;

second access port means for providing a substantially axially aligned access to said flow path by a second catheter means adapted for providing said other treatment; and third access port means, positioned adjacent one of the first and second access port means, for providing introduction of a lavage fluid in conjunction with said one of the first and second access port means;

an access control means for selectively positioning one or the other of said first and second access port means in substantial axial alignment with said flow path;

first catheter means, connected to said first access port means, for aspirating a respiratory tract when desired, said first catheter means comprising an elongated aspirating catheter tube and a collapsible sheath surrounding the aspirating catheter tube, said elongated aspirating catheter tube being slidably positionable through said first access port means for substantially axially aligned entry through said flow path and into a proximal end of an endotracheal tube; and second catheter means, connected to said second access port means, for providing said other treatment when desired, said second catheter means comprising an elongated catheter treatment tube and a collapsible sheath surrounding the catheter treatment tube, said elongated catheter treatment tube being slidably positionable through said second access port means for substantially axially aligned entry through said flow path and into a proximal end of an endotracheal tube.

13. An adapter assembly as defined in claim 12 wherein said first catheter means comprises a distal end permanently connected to said first access port means.

14. An adapter assembly as defined in claim 13 wherein said second catheter means comprises a distal end permanently connected to said second access port means.

15. An adapter assembly as defined in claim 13 wherein said second catheter means comprises a distal end removably connected to said second access port means.

16. An adapter assembly as defined in claim 12 wherein said first catheter means comprises a distal end removably connected to said first access port means.

17. An adapter assembly as defined in claim 16 wherein said second catheter means comprises a distal end permanently connected to said second access port means.

18. An adapter assembly as defined in claim 16 wherein said second catheter means comprises a distal end removably connected to said second access port means.

19. An adapter assembly as defined in claim 12 wherein said access control means comprises a stator means having an opening therethrough that is in substantial axial alignment with said flow path, and rotor means having said first and second access port means mounted thereon, said rotor means being rotatable to a first position wherein said first access port means is in fluid communication and is aligned with said stator opening and said second access port means is not in fluid communication and is not in alignment with said stator opening, and said rotor means being rotatable to a second position wherein said second access port means is in fluid communication and is aligned with said stator opening and said first access port means is not in fluid communication and is not in alignment with said stator opening.

24

20. An adapter assembly as defined in claim 19 wherein said rotor means is rotatable to a third position wherein neither of said first and second access port means are in fluid communication and are not in alignment with said stator opening.

21. An adapter assembly as defined in claim 12 wherein said adapter means comprises a first adapter having a distal port for releasable connection to a proximal end of an endotracheal tube, and a proximal port, and further comprising a second adapter having a distal end with means for releasable coupling to the proximal port of the first adapter, and wherein the proximal port means adapted for removable coupling to a ventilator and the first and second access port means are each formed as part of the second adapter.

22. An adapter assembly as defined in claims 20 or 21 wherein said first catheter means comprises a distal end removably connected to said first access port means.

23. An adapter assembly as defined in claim 22 wherein said second catheter means comprises a distal end permanently connected to said second access port means.

24. An adapter assembly as defined in claim 22 wherein said second catheter means comprises a distal end removably connected to said second access port means.

25. An adapter assembly as defined in claims 12 or 20 further comprising fourth access port means, positioned adjacent the other of said first and second access port means and essentially normal thereto, for providing introduction of a lavage fluid in conjunction with said other of the first and second access port means.

26. An adapter assembly as defined in claims 20 or 21 wherein said first catheter means comprises a distal end permanently connected to said first access port means.

27. An adapter assembly as defined in claim 26 wherein said second catheter means comprises a distal end permanently connected to said second access port means.

28. An adapter assembly as defined in claim 26 wherein said second catheter means comprises a distal end removably connected to said second access port means.

29. An adapter assembly for connection to a proximal end of an endotracheal tube and to a ventilator so as to provide ventilation of an intubated patient's respiratory tract, and for delivering respiratory therapy by way of aspiration of fluids and by way of other treatment including any one of delivery of fluids, removing patient samples or providing visual inspection of the respiratory tract through the endotracheal tube without interruption of ventilation, said adapter assembly comprising:

adapter means for providing a flow path therethrough which is substantially axial aligned with and adapted for fluid communication with a proximal end of an endotracheal tube, said adapter means comprising:

a distal port means adapted for removable coupling to a proximal end of an endotracheal tube;

proximal port means adapted for removable coupling to a ventilator;

first access port means for providing a substantially axially aligned access to said flow path by a first catheter means for aspirating the respiratory tract;

second access port means for providing a substantially axially aligned access to said flow path by a second catheter means adapted for providing said other treatment; and third access port means, positioned adjacent the first access port means, for providing introduction of a lavage fluid in conjunction with the first access port means;

an access control means for selectively positioning one or the other of said first and second access port means in substantial axial alignment with said flow path;

first catheter means, permanently connected to said first access port means; for aspirating a respiratory tract when desired, said first catheter means comprising an elongated aspirating catheter tube and a collapsible sheath surrounding the aspirating catheter tube, said elongated aspirating catheter tube being slidably positionable through said first access port means for substantially axially aligned entry through said flow path and into a proximal end of an endotracheal tube; and second catheter means, permanently connected to said second access port means, for providing said other treatment when desired, said second catheter means comprising elongated catheter treatment tube and a collapsible sheath surrounding the catheter treatment tube, said elongated catheter treatment tube being slidably positionable through said second access port means for substantially axially aligned entry through said flow path and into a proximal end of an endotracheal tube.

30. An adapter assembly for connection to a proximal end of an endotracheal tube and to a ventilator so as to provide ventilation of an intubated patient's respiratory tract, and for delivering respiratory therapy by way of aspiration of fluids and by way of other treatment including any one of delivery of fluids, removing patient samples or providing visual inspection of the respiratory tract through the endotracheal tube without interruption of ventilation, said adapter assembly comprising:

adapter means for providing a flow path therethrough which is substantially axially aligned with and adapted for fluid communication with a proximal end of an endotracheal tube, said adapter means comprising:

a distal port means adapted for removable coupling to a proximal end of an endotracheal tube;

proximal port means adapted for removable coupling to a ventilator;

first access port means for providing a substantially axially aligned access to said flow path by a first catheter means for aspirating a respiratory tract;

second access port means for providing a substantially axially aligned access to said flow path by a second catheter means adapted for providing said other treatment;

third access port means, positioned adjacent the first access port means, for providing introduction of a lavage fluid in conjunction with the first access port means; and fourth access port means, positioned adjacent the second access port means, for providing introduction of a lavage fluid in conjunction with the second access port means;

an access control means for selectively positioning one or the other of said first and second access port means in substantial axial alignment with said flow path;

first catheter means, removably connected to said first access port means, for aspirating a respiratory tract when desired, said first catheter means comprising an elongated aspirating catheter tube and a collapsible sheath surrounding the aspirating catheter tube, said elongated aspirating catheter tube being slidably positionable through said first access port means for substantially axially aligned entry through said flow path and into a proximal end of an endotracheal tube; and second catheter means, removably connected to said second access port means, for providing said other treatment when desired, said second catheter means comprising an elongated catheter treatment tube and a collapsible sheath surrounding the catheter treatment tube, said elongated catheter treatment tube being slidably positionable through said second access port means for substantially axially aligned entry through said flow path and into a proximal end of an endotracheal tube.

31. An adapter assembly as defined in claim 30 wherein said adapter means comprises a first adapter having a distal port for releasable connection to a proximal end of an endotracheal tube, and a proximal port, and further comprising a second adapter having a distal end with means for releasable coupling to the proximal port of the first adapter, and wherein the proximal port means adapted for removable coupling to a ventilator and the first and second access port means are each formed as part of the second adapter.

32. An adapter assembly for connection to a proximal end of an endotracheal tube and to a ventilator so as to provide ventilation of an intubated patient's respiratory tract, and for delivering respiratory therapy by way of aspiration of fluids and by way of other treatment including any one of delivery of fluids, removing patient samples or providing visual inspection of the respiratory tract through the endotracheal tube without interruption of ventilation, said adapter assembly comprising:

adapter means for providing a flow path therethrough which is substantially axially aligned with and adapted for fluid communication with a proximal end of an endotracheal tube, said adapter means comprising:

a distal port means adapted for removable coupling to a proximal end of a endotracheal tube;

proximal port means adapted for removable coupling to a ventilator;

first access port means for providing a substantially axially aligned access to said flow path by a first catheter means for aspirating a respiratory tract;

second access port means for providing a substantially axially aligned access to said flow path by a second catheter means adapted for providing said other treatment; and third access port means, positioned adjacent the first access port means, for providing introduction of a lavage fluid in conjunction with the first access port means; and access control means for selectively positioning one or the other of said first and second access port means in substantial axial alignment with said flow path, said access control means comprising a stator means having an opening therethrough that is in substantial axial alignment with said flow path, and rotor means having said first and second access port means mounted thereon, said rotor means being rotatable to a first position wherein said first access port means is in fluid communication and is aligned with said stator opening and said second access port means is not in fluid communication and is not in alignment with said stator opening, and said rotor means being rotatable to a second position wherein said second access port means is in fluid communication and is aligned with said stator opening and said first access port means is not in fluid communication and is not in alignment with said stator opening, and wherein said rotor means is rotatable to a third position wherein neither of said first and second access port means are in fluid communication and are not in alignment with said stator opening;

first catheter means, removably connected to said first access port means, for aspirating a respiratory tract when desired, said first catheter means comprising an elongated aspirating catheter tube and a collapsible sheath surrounding the aspirating catheter tube, said elongated aspirating catheter tube being slidably positionable through said first access port means for substantially axially aligned entry through said flow path and into a proximal end of an endotracheal tube; and second catheter means, removably connected to said second access port means, for providing said other treatment when desired, said second catheter means comprising an elongated catheter treatment tube and a collapsible sheath surrounding the catheter treatment tube, said elongated catheter treatment tube being slidably positionable through said second access port means for substantially axially aligned entry through said flow path and into a proximal end of an endotracheal tube.

33. An adapter assembly for connection to a proximal end of an endotracheal tube and to a ventilator so as to provide ventilation of an intubated patient's respiratory tract, and for delivering respiratory therapy by way of aspiration of fluids, said adapter assembly comprising:

adapter means for providing a flow path therethrough which is substantially axially aligned with and adapted for fluid communication with a proximal end of an endotracheal tube, said adapter means comprising:
a distal port means adapted for removable coupling to a proximal end of an endotracheal tube;
proximal port means adapted for removable coupling to a ventilator; and
first access port means for providing a substantially axially aligned access to said flow path by a catheter means for aspirating a respiratory tract;

access control means for selectively positioning said first access port means either in a first position where said first access port means is in substantial axial alignment with said flow path or in a second position where said first access port means is not in substantial axial alignment with said flow path; and catheter means, connected to said first access port means, for aspirating a respiratory tract when desired, said catheter means being slidably positionable through said first access port means for substantially axially aligned entry through said flow path and a proximal end of an endotracheal tube.

34. An adapter assembly as defined in claim 33 wherein said access control means comprises a stator means having an opening therethrough that is in substantial axial alignment with said flow path, and means rotor having said first access port means mounted thereon, said rotor means being rotatable to a first position wherein said first access port means is in fluid communication and is aligned with said stator opening and said rotor means being rotatable to a second position wherein said first access port means is not in fluid communication and is not in alignment with said stator opening.

35. An adapter assembly as defined in claim 33 wherein said catheter means comprises a distal end removably connected to said first access port means.

36. An adapter assembly as defined in claim 33 further comprising second access port means, positioned adjacent said first access port means and essentially normal thereto, for providing introduction of a lavage fluid in conjunction with said first access port means.

37. An adapter assembly as defined in claim 33 wherein said adapter means comprises a first adapter having a distal port for releasable connected to a proximal end of an endotracheal tube, and a proximal port, and further comprising a second adapter having a distal end with means for releasable coupling to the proximal port of the first adapter, and wherein the proximal port means adapted for removable coupling to a ventilator and the first access port means are each formed as part of the second adapter.

38. An adapter assembly for connection to a proximal end of an endotracheal tube and to a ventilator so as to provide ventilation of an intubated patient's respiratory tract, and for delivering respiratory therapy by way of aspiration of fluids, said adapter assembly comprising:

adapter means for providing a flow path therethrough which is substantially axially aligned with and adapted for fluid communication with a proximal end of an endotracheal tube, said adapter means comprising:
a distal port means adapted for removable coupling to a proximal end of an endotracheal tube;
proximal port means adapted for removable coupling to a ventilator;
first access port means for providing a substantially axially aligned access to said flow path by a catheter means for aspirating a respiratory tract; and
second access port means, positioned adjacent the first access port means, for providing introduction of a lavage fluid in conjunction with the first access port means;

access control means for selectively positioning said first access port means in substantial axial alignment with said flow path, access control means comprising a stator means having an opening therethrough that is in substantial axial alignment with said flow path, and rotor means having said first access port means mounted thereon, said rotor means being rotatable to a first position wherein said first access port means is in fluid communication and is aligned with said stator opening and said rotor means being rotatable to a second position wherein said first access port means is not in fluid communication and is not in alignment with said stator opening; and catheter means, removably connected to said first access port means, for aspirating a respiratory tract when desired, said catheter means comprising an elongated aspirating catheter tube and a collapsible sheath surrounding the aspirating catheter tube, said elongated aspirating catheter tube being slidably positionable through said first access port means for substantially axially aligned entry through said flow path and into a proximal end of an endotracheal tube.

* * * * *